United States Patent
Hecker et al.

(10) Patent No.: US 10,662,205 B2
(45) Date of Patent: May 26, 2020

(54) CYCLIC BORONIC ACID ESTER DERIVATIVES AND THERAPEUTIC USES THEREOF

(71) Applicant: Rempex Pharmaceuticals, Inc., San Diego, CA (US)

(72) Inventors: Scott Hecker, Del Mar, CA (US); Raja K. Reddy, San Diego, CA (US); Tomasz Glinka, Cupertino, CA (US)

(73) Assignee: QPEX BIOPHARMA, INC., San Diego, CA (US)

( * ) Notice: Subject to any disclaimer, the term of this patent is extended or adjusted under 35 U.S.C. 154(b) by 265 days.

(21) Appl. No.: 15/527,687

(22) PCT Filed: Nov. 13, 2015

(86) PCT No.: PCT/US2015/060556
§ 371 (c)(1),
(2) Date: May 17, 2017

(87) PCT Pub. No.: WO2016/081297
PCT Pub. Date: May 26, 2016

(65) Prior Publication Data
US 2019/0084999 A1 Mar. 21, 2019

Related U.S. Application Data

(60) Provisional application No. 62/081,136, filed on Nov. 18, 2014.

(51) Int. Cl.
*A61K 31/69* (2006.01)
*C07F 5/02* (2006.01)
*A61K 45/06* (2006.01)
*A61P 31/04* (2006.01)

(52) U.S. Cl.
CPC .............. *C07F 5/025* (2013.01); *A61K 31/69* (2013.01); *A61K 45/06* (2013.01); *A61P 31/04* (2018.01)

(58) Field of Classification Search
None
See application file for complete search history.

(56) References Cited

U.S. PATENT DOCUMENTS

| | | | |
|---|---|---|---|
| 3,686,398 A | 8/1972 | Kohn et al. | |
| 4,194,047 A | 3/1980 | Christensen et al. | |
| 4,260,543 A | 4/1981 | Miller | |
| 4,353,807 A | 10/1982 | Braid | |
| 4,409,214 A | 10/1983 | Takaya et al. | |
| 4,822,786 A | 4/1989 | Zama et al. | |
| 5,442,100 A | 8/1995 | Bjorkquiest et al. | |
| 5,888,998 A | 3/1999 | Maiti et al. | |
| 6,184,363 B1 | 2/2001 | Shoichet et al. | |
| 6,586,615 B1 | 7/2003 | Kettner et al. | |
| 7,271,186 B1 | 9/2007 | Shoichet et al. | |
| 7,439,253 B2 | 10/2008 | Lampilas et al. | |
| 7,582,621 B2 | 9/2009 | Baker et al. | |
| 7,612,087 B2 | 11/2009 | Aszodi et al. | |
| 7,674,913 B2 | 3/2010 | Campbell et al. | |
| 7,825,139 B2 | 11/2010 | Campbell et al. | |
| 8,680,136 B2 | 3/2014 | Hirst et al. | |
| 9,012,491 B2 | 4/2015 | Reddy et al. | |
| 9,101,638 B2 | 8/2015 | Reddy et al. | |
| 9,132,140 B2 | 9/2015 | Reddy et al. | |
| 9,156,858 B2 | 10/2015 | Reddy et al. | |
| 9,241,947 B2 | 1/2016 | Reddy et al. | |
| 9,296,763 B2 | 3/2016 | Hirst et al. | |
| 9,511,142 B2 | 12/2016 | Burns et al. | |
| 9,642,869 B2 | 5/2017 | Reddy et al. | |
| 9,687,497 B1 | 6/2017 | Bis et al. | |
| 9,694,025 B2 | 7/2017 | Hirst et al. | |
| 10,004,758 B2 | 6/2018 | Hirst et al. | |
| 2004/0019203 A1 | 1/2004 | Micetich et al. | |
| 2004/0157826 A1 | 8/2004 | Lampilas et al. | |
| 2005/0020572 A1 | 1/2005 | Aszodi et al. | |
| 2005/0070719 A1 | 3/2005 | Belyakov et al. | |
| 2006/0019116 A1 | 1/2006 | Conley et al. | |
| 2006/0178357 A1 | 8/2006 | Buynak et al. | |
| 2006/0210883 A1 | 9/2006 | Chen et al. | |
| 2010/0056478 A1 | 3/2010 | Desarbre et al. | |
| 2010/0120715 A1 | 5/2010 | Burns et al. | |
| 2010/0256092 A1 | 10/2010 | Xia et al. | |
| 2010/0292185 A1 | 11/2010 | Burns et al. | |
| 2011/0288063 A1 | 11/2011 | Maiti et al. | |
| 2012/0040932 A1 | 2/2012 | Hirst et al. | |
| 2013/0316978 A1 | 11/2013 | Reddy et al. | |
| 2013/0331355 A1 | 12/2013 | Griffith et al. | |
| 2013/0345172 A1 | 12/2013 | Hirst et al. | |

(Continued)

FOREIGN PATENT DOCUMENTS

| | | |
|---|---|---|
| EP | 1550657 A1 | 7/2005 |
| EP | 2508506 A1 | 10/2012 |

(Continued)

OTHER PUBLICATIONS

Ambrose et al., Pharmacokinetics-pharmacodynamics of antimicrobial therapy: it's not just for mice anymore. Clin Infect Dis. (2007) 44: 79-86.

Ambrose et al., "Pharmacokinetics-pharmacodynamics of CB-618 in combination with cefepime, ceftazidime, ceftolozane and meropenem: the pharmacological basis for a stand-alone beta-lactamase inhibitor", Antimicrob Agents Chemother. (Nov. 2017) 61(12): e00630-17; 7 pages.

Austad et al. "Development of a multi kilogram-scale, tandem cyclopropanation ring-expansion reaction en route to hedgehog antagonist IPI-926", Org Process Res Dev., (2016) 20(4):786-798; Supporting Information, 70 pages.

(Continued)

*Primary Examiner* — Samantha L Shterengarts
(74) *Attorney, Agent, or Firm* — Knobbe, Martens, Olson & Bear, LLP

(57) ABSTRACT

Disclosed herein are antimicrobial compounds, compositions, pharmaceutical compositions, and the use and preparation thereof. Some embodiments relate to cyclic boronic acid ester derivatives and their use as therapeutic agents.

35 Claims, No Drawings

(56) References Cited

U.S. PATENT DOCUMENTS

| | | |
|---|---|---|
| 2014/0194284 A1 | 7/2014 | Reddy et al. |
| 2014/0194381 A1 | 7/2014 | Reddy et al. |
| 2014/0194382 A1 | 7/2014 | Reddy et al. |
| 2014/0194385 A1 | 7/2014 | Reddy et al. |
| 2014/0194386 A1 | 7/2014 | Burns et al. |
| 2014/0206648 A1 | 7/2014 | Reddy et al. |
| 2014/0274954 A1 | 9/2014 | Chellappan et al. |
| 2015/0119363 A1 | 4/2015 | Dudley et al. |
| 2016/0220591 A1 | 8/2016 | Hirst et al. |
| 2016/0339045 A1 | 11/2016 | Griffith et al. |
| 2017/0057979 A1 | 3/2017 | Hecker et al. |
| 2017/0088561 A1 | 3/2017 | Reddy et al. |
| 2017/0136047 A1 | 5/2017 | Reddy et al. |
| 2017/0173055 A1 | 6/2017 | Bis et al. |
| 2018/0002351 A1 | 1/2018 | Hecker et al. |
| 2018/0051041 A1 | 2/2018 | Hecker et al. |
| 2018/0071325 A1 | 3/2018 | Hirst et al. |
| 2018/0207183 A1 | 7/2018 | Hirst et al. |
| 2018/0214465 A1 | 8/2018 | Hirst et al. |

FOREIGN PATENT DOCUMENTS

| | | |
|---|---|---|
| FR | 2573070 A1 | 5/1986 |
| JP | 2003-229277 | 8/2003 |
| JP | 2004-291253 | 10/2004 |
| WO | WO 1987/05297 | 9/1987 |
| WO | WO 1989/10961 | 11/1989 |
| WO | WO 1998/56392 A1 | 12/1998 |
| WO | WO 2000/035904 A1 | 6/2000 |
| WO | WO 2000/035905 A1 | 6/2000 |
| WO | WO 2001/023374 A1 | 4/2001 |
| WO | WO 2001/030149 | 5/2001 |
| WO | WO 2002/022137 A1 | 3/2002 |
| WO | WO 2002/083884 | 10/2002 |
| WO | WO 2003/070714 | 8/2003 |
| WO | WO 2004/039859 | 5/2004 |
| WO | WO 2004/058679 A2 | 7/2004 |
| WO | WO 2004/064755 A2 | 8/2004 |
| WO | WO 2005/033090 | 4/2005 |
| WO | WO 2005/035532 A1 | 4/2005 |
| WO | WO 2005/087700 | 9/2005 |
| WO | WO 2006/052733 A1 | 5/2006 |
| WO | WO 2006/091771 | 8/2006 |
| WO | WO 2007/058602 A2 | 5/2007 |
| WO | WO 2007/065288 A2 | 6/2007 |
| WO | WO 2007/095638 | 8/2007 |
| WO | WO 2008/039420 A2 | 4/2008 |
| WO | WO 2008/116813 A1 | 10/2008 |
| WO | WO 2009/046098 A1 | 4/2009 |
| WO | WO 2009/064413 A1 | 5/2009 |
| WO | WO 2009/064414 A1 | 5/2009 |
| WO | WO 2009/091856 A1 | 7/2009 |
| WO | WO 2009/117540 A1 | 9/2009 |
| WO | WO 2009/139834 A1 | 11/2009 |
| WO | WO 2009/140309 A2 | 11/2009 |
| WO | WO 2010/056827 A1 | 5/2010 |
| WO | WO 2010/075286 A1 | 7/2010 |
| WO | WO 2010/097675 A1 | 9/2010 |
| WO | WO 2010/130708 A1 | 11/2010 |
| WO | WO 2010/144338 A1 | 12/2010 |
| WO | WO 2011/017125 A1 | 2/2011 |
| WO | WO 2011/103686 A1 | 9/2011 |
| WO | WO 2011/123502 A1 | 10/2011 |
| WO | WO 2011/154953 | 12/2011 |
| WO | WO 2012/021455 | 2/2012 |
| WO | WO 2012/058065 A1 | 5/2012 |
| WO | WO 2012/067664 A1 | 5/2012 |
| WO | WO 2012/106995 A1 | 8/2012 |
| WO | WO 2012/136383 A1 | 10/2012 |
| WO | WO 2013/033461 A1 | 3/2013 |
| WO | WO 2013/053372 A1 | 4/2013 |
| WO | WO 2013/056163 A1 | 4/2013 |
| WO | WO 2013/092979 A1 | 6/2013 |
| WO | WO 2013/104774 A1 | 7/2013 |
| WO | WO 2013/104897 A1 | 7/2013 |
| WO | WO 2013/122888 | 8/2013 |
| WO | WO 2013/184845 A1 | 12/2013 |
| WO | WO 2014/089365 A1 | 6/2014 |
| WO | WO 2014/107535 A1 | 7/2014 |
| WO | WO 2014/107536 A1 | 7/2014 |
| WO | WO 2014/110442 A1 | 7/2014 |
| WO | WO 2014/144380 A1 | 9/2014 |
| WO | WO 2014/151958 A1 | 9/2014 |
| WO | WO 2015/171398 A1 | 11/2015 |
| WO | WO 2015/171430 A1 | 11/2015 |
| WO | WO 2015/179308 A1 | 11/2015 |
| WO | WO 2015/191907 A1 | 12/2015 |
| WO | WO 2016/003929 A1 | 1/2016 |
| WO | WO 2016/065282 A1 | 4/2016 |

OTHER PUBLICATIONS

Berkhout et al., "Pharmacodynamics of Ceftazidime and Avibactam in Neutropenic Mice with Thigh or Lung Infection", Antimicrob Agents Chemother. (2015) 60 (1): 368-375.

Bhavani et al., Pharmacokinetic-Pharmacodynamic (PK_PD) basis for CLSI carbapenem (CARB) susceptibility breakpoint changes. abstr Abstracts of Papers, 50th Interscience Conference on Antimicrobial Agents and Chemotherapy, Sep. 12-15, 2010; #A1-1382, Boston, MA; 3 pages.

Bilello et al., "Effect of 2',3'-8 didehydro-3'-deoxythymidine in an in vitro hollow-fiber pharmacodynamic model system correlates with results of dose-ranging clinical studies", Antimicrob Agents Chemother. (1994) 38(6): 1386-1391.

Bowker et al., Comparative pharmacodynamics of meropenem using an in-vitro model to simulate once, twice and three times daily dosing in humans. J Antimicrob Chemother (1998) 42: 461-467.

Braisted et al., "Discovery of a potent small molecule IL-2 inhibitor through fragment assembly", J Am Chem Soc., (2003) 125(13): 3714-3715; Supporting Information, 42 pages.

Bulik et al., "Comparison of the activity of a human simulated, high-dose, prolonged infusion of meropenem against Klebsiella pneumoniae producing the KPC carbapenemase versus that against Pseudomonas aeruginosa in an in vitro pharmacodynamic model", Antimicrob Agents Chemother (2010) 54(2): 804-810.

Bundgaard H. [Ed.], "Design of Prodrugs", Elsevier (1985); TOC, 2 pages.

CAS Registry No. 831209-98-4 6H-Dibenz[c,e][1,2]oxaborin, 6a, 10a-dihydro-6-hydroxy; Entered STN: Feb. 15, 2005; 1 page.

CAS Registry No. 831210-03-8 6H-Dibenz[c,e][1,2]oxaborin, 2,4-dibromo-6a, 10a-dihydro-6-hydroxy; Feb. 15, 2005; 1 page.

CAS Registry No. 2114651-20-4; "7-Benzofurancarboxylic acid", Aurora Fine Chemicals; Aug. 16, 2017; 1 page.

CAS Registry No. 1780853-40-8; "7-Benzofurancarboxylic acid", Aurora Fine Chemicals; Jun. 15, 2015; 1 page.

CAS Registry No. 1427326-65-5; "7-Benzofurancarboxylic acid", Ellanova Laboratories; Apr. 5, 2013; 1 page.

CAS Registry No. 1344904-36-4; "7-Benzofurancarboxylic acid", Asiba Pharmatech, Inc.; Nov. 13, 2011; 1 page.

CAS Registry No. 1890373-92-8; "Benzoic acid", Aurora Fine Chemicals; Apr. 15, 2016; 1 page.

Chandrasekhar et al., "The first Corey-Chaykovsky epoxidation and cyclopropanation in ionic liquids", Tetrahedron Letts. (2003) 44:3629-3630.

Charette et al., "Palladium-catalyzed Suzuki-type cross-couplings of iodocyclopropanes with boronic acids: Synthesis of trans-1,2-dicyclopropyl alkenes", J Org Chem. (1996) 61(25): 8718-8719; Supporting Information, 52 pages.

Cheng et al., "Inhibitors of hepatitis C virus polymerase: Synthesis and characterization of novel 2-oxy-6-fluoro-N-((S)-1-hydroxy-3-phenylpropan-2-yl)-benzamides", Bioorg Med Chem Ltts. (2010) 20:2119-2124.

Chinchilla et al., "Recent advances in Sonogashira reactions", Chem Soc Rev., (2011) 40: 5084-5121.

Clark et al., "Concise synthesis of the C-1-C-12 fragment of amphidinolides T1-T5", Org Biomol Chem. (2011) 9(13): 4823-4830.

(56) References Cited

OTHER PUBLICATIONS

Clinical and Laboratory Standards Institute (formerly NCCLS, National Committee for Clinical Laboratory Standards). "Methods for Dilution of Antimicrobial Susceptibility Tests for Bacteria That Grow Aerobically; Approved Standard—9th Edition", CLSI (Jan. 2012) M07-A9 32(2): 88 pages.

Craig WA., "Pharmacokinetic/pharmacodynamic parameters: rationale for antibacterial dosing of mice and men", Clin Infect Dis. (1998) 26(1): 1-10.

Dörwald F.Z., Side Reactions in Organic Synthesis—A guide to Successful Synthesis Design, Wiley-VCH Verlag GmbH & Co. KGaA, Weinheim, Germany (2005); Preface in 4 pages.

Drusano et al., Meropenem: clinical response in relation to in vitro susceptibility. Clin Microbiol Infect. (2000) 6: 185-194.

Dunetz et al., "Large-scale applications of amide coupling reagents for the synthesis of pharmaceuticals", Org Process Res Develop. (2016) 20(2): 140-177.

Eggen et al., "Total synthesis of cryptophycin-24 (Arenastatin A) amenable to structural modifications in the C16 side chain", J Org Chem. (2000) 65(23): 7792-7799; and Supporting documents, 22 pages.

Goodman et al., [Eds.], "The Pharmacological Basis of Therapeutics", 8th. Edition, Pergamon Press (1990); TOC, 8 pages.

Gunanathan et al., "Ruthenium catalyzed hydroboration of terminal alkynes to Z vinylboronates", J Am Chem Soc. (2012) 134(35): 14349-14352; Supporting Information, 32 pages.

He et al., "Ligand-promoted borylation of C(sp3)—H bonds with palladium(II) catalysts", Angew Chem Int Ed., (2016) 55(2): 785-789.

Higuchi et al., [Eds.] "Pro-drugs as Novel Drug Delivery Systems", ACS Sumposium Series 14 (1975); TOC, 3 pages.

Hu et al., "Ag(I)-catalyzed C—H borylation of terminal alkynes", Tetrahedron (2014) 70: 5815-5819.

Ishiyama et al., "Palladium(0)-catalyzed cross-coupling reaction of alkoxydiboron with haloarenes: A direct procedure for arylboronic esters", J Org Chem. (1995) 60(23): 7508-7510; Supporting Information, 35 pages.

Jang et al., Copper-catalyzed trans-hydroboration of terminal aryl alkynes: Stereodivergent synthesis of alkenylboron compounds. Org Letts. (2016) 18(6): 1390-1393; Supporting Information in 37 pages.

Jordan V.C., "Tamoxifen: A most unlikely pioneering medicine", Drug Discovery (2003) 2:205-213.

Kuang et al., "Convenient and stereoselctive synthesis of (Z)-1-bromo-1-alkenes by microwave-induced reaction", Tetrahedron Letts. (2001) 42(23): 3893-3896.

Lebel et al., "Boc-protected amines via a mild and efficient one-pot Curtius rearrangement", Org Letts. (2005) 7(19): 4107-4110.

Lee et al., "Comparison of 30-min and 3-h infusion regimens for imipenem/cilastatin and for meropenem evaluated by Monte Carlo simulation", Diagn Microbiol Infect Dis. (2010) 68: 251-258.

Li et al., "Population Pharmacokinetic Analysis and Dosing Regimen Optimization of Meropenem in Adult Patients", J Clin Pharmacol. (2006) 46(10): 1171-1178.

Lin et al., "Enantioselective syn and anti homocrotylation of aldehydes: Application to the formal synthesis of spongidepsin", J Am Chem Soc. (2015) 137(40): 13176-13182; Supporting Information, 177 pages.

Louie et al., Impact of meropenem in combination with tobramycin in a murine model of Pseudomonas aeruginosa pneumonia. Antimicrob Agents Chemother. (2013) 57: 2788-2792.

Luithle et al., "Synthesis of enantiomerically pure cis-cyclopropylboronic esters", Eur J Org Chem. (2000) 14: 2557-2562.

MacVane et al., Characterizing in vivo pharmacodynamics of carbapenems against Acinetobacter baumannii in a Murine thigh infection model to support breakpoint determinations. Antimicrob Agents Chemother (2014) 58: 599-601.

Maguire B. A., Inhibition of Bacterial Ribosome Assembly: a Suitable Drug Target? Microbiol Mol Biol Rev. (2009) 73(1):22-35.

McSharry et al., "Prediction of the pharmacodynamically linked variable of oseltamivir carboxylate for influenza A virus using an in vitro hollow-fiber infection model system", Antimicrob Agents Chemother (2009) 53(6): 2375-2381.

Mkhalid et al., "C—H activation for the construction of C—B bonds", Chem Rev. (2010) 110(2): 890-931.

Molander et al., "Highly stereoselective synthesis of cis-alkenyl pinacolboronates and potassium cis-alkenyltrifluoroborates via a hydroboration/protodeboronation approach", J Org Chem. (2008) 73(17): 6841-6844.

Mori et al., "Synthesis of 1,3-dienes from alkynes and ethylene: Acetic acid 2-methylene-3-phenethylbut-3-enyl ester", Org Synth. 2005 81: 1-13.

Morrill et al., "Treatment Options for Carbapenem-Resistant Enterobacteriaceae Infections", Open Forum Infectious Diseases [OFID] Apr. 2015; 15 pages.

Nicasio et al., "Pharmacokinetics-Pharmacodynamics of Tazobactam in Combination with Piperacillin in an In Vitro Infection Model", Antimicrob Agents Chemother. (2016) 60: 2075-2080. doi: 10.1128/AAC.02747-15.

Nicolau DP., "Pharmacokinetic and pharmacodynamic properties of meropenem", Clin Infect Dis. (2008) 47 Suppl 1: S32-S40.

Noguchi et al., "Boron-masking strategy for the selective synthesis of oligoarenes via iterative Suzuki-Miyaura coupling", J Am Chem Soc. (2007) 129(4): 758-759; Supporting Information, 46 pages.

Pellissier, H., "Recent developments in asymmetric cyclopropanation", Tetrahedron (2008) 64(30-31): 7041-7095.

Pietruszka et al., "Enantiomerically pure cyclopropylamines from cyclopropylboronic esters", Eur J Org Chem. (2009) 34: 5998-6008.

Pine et al., "Resonance vs. Tautomerism" in Organic Chemistry; McGraw-Hill, New York 4th Ed. (1980), pp. 218-219.

Rehm et al., "*Staphylococcus aureus*: Methicillin-susceptible *S. aureus* to Methicillin-resistant *S. aureus* and Vancomycin-resistant *S. aureus*", Clin Inf Diseases. (2010) 51(S2):S176-S182.

Roche, E.B. (Ed.) Bioreversible Carriers in Drug Design: Theory and Application. New York: Pergamon Press (1987); pp. 14-21.

Rubino et al., "Phase 1 Study of the Safety, Tolerability, and Pharmacokinetics of Vaborbactam and Meropenem Alone and in Combination following Single and Multiple Doses in Healthy Adult Subjects", Antimicrob Agents Chemother. (Apr. 2018) 62(4): E02228-17; 12 pages.

Sabet et al., "Activity of Simulated Human Dosage Regimens of Meropenem and Vaborbactam against Carbapenem-Resistant Enterobacteriaceae in an In Vitro Hollow-Fiber Model", Antimicrob Agents Chemother (2017) 62. pii: e01969-17. doi: 10.1128/AAC.01969-17.

Sabet et al., "Activity of Meropenem-Vaborbactam in Mouse Models of Infection Due to KPC-Producing Carbapenem-Resistant Enterobacteriaceae", Antimicrob Agents Chemother. (2017) 62:1 10 e01446-379 17.

Scriven et al., "Azides: Their preparation and synthetic uses", Chem Rev. (1988) 88(2): 297-368.

Singh et al., "Confronting the challenges of discovery of novel antibacterial agents", Bioorg Med Chem Lett. (2014) 24(16):3683-3689.

Sumida et al., "Boron-selective biaryl coupling approach to versatile dibenzoxaborins and application to concise synthesis of defucogilvocarcin M", Org Ltt. (Dec. 2014) 16(23):6240-6243.

Sun et al., "A method for the deprotection of alkylpinacolyl boronate esters", J Org Chem. (2011) 76(9): 3571-3575; Supporting Information, 8 pages.

Tam et al., "Optimization of meropenem minimum concentration/MIC ratio to suppress in vitro resistance of Pseudomonas aeruginosa", Antimicrob Agents Chemother. (2005) 49(12): 4920-4927.

U.S. Department of Health and Human Resources, "Antibiotic Resistance Threats in the United States, 2013"; 114 pages.

Valters et al., "Ring-Chain Tautomerism", Plenum Press, New York and London, Softcover reprint of the hardcover 1st Ed. 1985, Chapter 1, 23 pages.

VanScoy et al., "Pharmacokinetics-pharmacodynamics of tazobactam in 386 combination with ceftolozane in an in vitro infection model", Antimicrob Agents Chemother. (2013) 57: 2809-2814. doi: 10.1128/AAC.02513-12.

(56) References Cited

OTHER PUBLICATIONS

Voituriez et al., "Preparation of a storable zinc carbenoid species and its application in cyclopropanation, chain extension, and [2,3]-sigmatropic rearrangement reactions", J Org Chem. (2010) 75(4): 1244-1250; Supporting Information, 20 pages.
Walker et al., "Pharmacodynamic activities of meropenem in an animal infection model", (1994), Abstracts of Papers #A91, 34th Interscience Conference on Antimicrobial Agents and Chemotherapy, Orlando, FL., 5 pages.
Wilson D.N., "The A-Z of bacterial translation inhibitors", Crit Rev Biochem Mol Biolog. (2009) 44(6):393-433.
Wong et al., "A chemoselective Reformatsky-Negishi approach to α-haloaryl esters", Tetrahedron (2014) 70(7): 1508-1515.
Zhu et al., "Design, preparation, x-ray crystal structure, and reactivity of o-alkoxyphenyliodonium bis(methoxycarbonyl)methanide, a highly soluble carbene precursor", Org Lett. (2012) 14(12): 3170-3173; Supporting Information, 76 pages.
Abdel-Magid et al., "Reductive Amination of Aldehydes and Ketones with Sodium Triacetoxyborohydride: Studies on Direct and Indirect Reductive Amination Procedures", J Org Chem. (1996) 61(11):3849-3862.
Adediran et al., "A 'cephalosporin-like' cyclic depsipeptide: Synthesis and reaction with beta-lactam-recognizing enzymes", Bioorg Med Chem Lett. (1999) 9(3):341-346.
Aizpurua et al., "Synthesis of benzyl halides from aldehydes promoted by halosilanes and 1,1,3,3-tetramethyldisiloxane (TMDS)", Tetrahedron Lett. (1984) 25(10):1103-1104.
Akiyama et al., "N-Hydroxy Amides. Part 6. Synthesis and Spectroscopic Properties of 1-Hydroxypiperazine-2,5-diones", J Chem Soc., Perkin Trans I, (1989) 2:235-239.
Allen et al., "Ansel's Pharmaceutical Dosage Forms and Drug Delivery Systems", 8th Edition (2004) TOC only.
American Chemical Society. STN Chemical Database Registry RN: 1226917; Jun. 2010; 2 pages.
Arya et al., "Advances in asymmetric enolate methodology", Tetrahedron (2000) 56:917-947.
Babic et al., "What's new in antibiotic resistance? Focus on beta-lactamases", Drug Res Updates (2006) 9:142-156.
Banker G.S. et al. [Eds.], Modern Pharmaceutics, 4th Edition; Marcel Dekker, Inc. (2002); Chapters 9 and 10, 98 pages.
Bassetti et al., "New antibiotics for bad bugs: where are we?", Ann Clin Microbiol Antimicrob. (2013) 12:22-36.
Becker, Daniel E., "Antimicrobial Drugs", Anesth Prog (2013) 60:111-123.
Beenen et al., "Asymmetric copper-catalyzed synthesis of alpha-amino boronate esters from N-tert-butanesulfinyl aldimines", J Am Chem Soc. (2008) 130(22):6910-6911.
Biedrzycki et al., "Derivatives of tetrahedral boronic acids", J. Organomet. Chem. (1992) 431:255-270.
Bou et al., "Cloning, nucleotide sequencing, and analysis of the gene encoding an AmpC beta-lactamase in Acinetobacter baumannii", Antimicrob Agents Chemother (2000) 44(2):428-432.
Bou et al., "OXA-24, a novel class D beta-lactamase with carbapenemase activity in an Acinetobacter baumannii clinical strain", Antimicrob Agents Chemother (2000) 44(6):1556-1561 and Erratum: Antimicrob Agents Chemother. (2006) 50(6) 2280.
Brabez et al., "Design,synthesis, and biological studies of efficient multivalent melanotropin ligands: tools toward melanoma diagnosis and treatment", J Med Chem. (2011) 54(20):7375-7384.
Brosz et al., "Resolution of alpha-aminoboronic esters by diastereoselective crystallization with pinanediols. Confirmation by x-ray analysis", Tetrahedron: Asymmetry (1997) 8(9):1435-1440.
Buesking et al., "Asymmetric Synthesis of Protected alpha-Amino Boronic Acid Derivatives with an Air- and Moisture-stable Cu(II) Catalyst", J Org Chem. (Mar. 2014) 79(8): 3671-3677.
Bush et al., "Minireview: Updated Functional Classification of beta-Lactamases," Antimicrob Agents Chemo. (2010) 54(3):969-976.
CAS Registry No. 2005:329437 CAPLUS; "Product subclass 28: Vinylboranes", Vaultier et al., (2004); XP-002764965; 1 page.

CAS Registry Nos. 69190-59/60 (2-(bis(phenylthio)methyl)-4,4,5,5-tetramethyl-1,3,2-dioxaborolane) and 69190-60-9 (2-(bis(phenylthio)methyl)-1,3,2-dioxaborinane) Scheme 18 (2015); 2 pages.
CAS Registry No. 105892-95-3 Boronic acid [1-(phenylsulfonyl)heptyl]-, dimethyl ester (2015); 2 pages.
Cheng et al., "Synthesis of Aryl Thioethers through the N-Chlorosuccinimide-Promoted Cross-Coupling Reaction of Thiols with Grignard Reagents", J Org Chem. (2012) 77(22):10369-10374.
Chemicalland21.com. "Meglumine", Jun. 7, 2011. Downloaded from </www.chemicalland21.com/lifescience/phar/N-METHYL-D-GLUCAMINE.htm>; 2 pages.
Clinical and Laboratory Standards Institute (formerly NCCLS, National Committee for Clinical Laboratory Standards). "Methods for Dilution of Antimicrobial Susceptibility Tests for Bacteria That Grow Aerobicaliy", CLSI (Jan. 2006) M7-A7 26(2), 64 pages.
Clinical and Laboratory Standards Institute (formerly NCCLS, National Committee for Clinical Laboratory Standards). "Methods for Dilution of Antimicrobial Susceptibility Tests for Bacteria That Grow Aerobicaliy", CLSI (Jan. 2009) M07-A8 29(2), 88 pages.
Clinical Trial NCT02168946, "A Phase 3, Multi-Center, Randomized, Open-Label Study of Carbavance (Meropenem/RPX7009) Versus Best Available Therapy in Subjects with Selected Serious Infections Due to Carbapenem-Resistant Enterobacteriaceae", Oct. 6, 2014; retrieved online from URL:https://clinicaltrials.gov/archive/NCT02168946/20140_10_06.
Conte et al., "Intrapulmonary pharmacokinetics and pharmacodynamics of meropenem", Int J Antimicrob Agents (Dec. 2005) 26(6):449-456.
Coppa et al., "A Facile, Convenient and Selective Homolytic Carbamoylation of Heteroaromatic Bases", Heterocycles (1993) 36(12):2687-2696.
Coutts et al., "Two Efficient Methods for the Cleavage of Pinanediol Boronate Esters Yielding the Free Boronic Acids", Tetrahedron Lett. (1994) 35(29):5109-5112.
Cunha, "Meropenem in elderly and renally impaired patients", Int'l J Antimicro Agents (1998) 10: 107-117.
Danziger et al., "Automated Site-directed Drug Design: A General Algorithm for Knowledge Acquisition about Hydrogen-bonding Regions at Protein Surfaces", Proc. Royal Soc London, Series B, Biol. Sciences (1989) 236(1283):101-113.
Darses et al., "Potassium Organotrifluoroborates: New Perspectives in organic Synthesis", Chem Rev. (2008) 108:288-325.
Davoli et al., "Enantioselective total synthesis of (-)-microcarpalide", Tetrahedron (2005) 61:4427-4436.
de Meijere a. [Ed], Science of Synthesis—vol. 24; "Three Carbon-Heteroatom Bonds: Ketene Acetals and Yne-X Compounds", TOC 46 pages.
Di Gioia et al., "Optically Pure N-Hydroxy-O-triisopropylsilyl-alpha-L-amino Acid Methyl Esters from AlCl3-Assisted Ring Opening of Chiral Oxaziridines by Nitrogen Containing Nucleophiles", J Org Chem. (2005) 70(25):10494-10501.
Drawz et al., "Three Decades of beta-Lactamase Inhibitors", Clin Microbiol Reviews (Jan. 2010) 23(1):160-201.
Eidam et al., "Design, synthesis, crystal structures and antimicrobial activity of sulfonamide boronic acids as beta-lactamase inhibitors", J Med Chem. (2010) 53(21):7852-7863.
Eissenstat et al., "Aminoalkylindoles: Structure-Activity Relationships of Novel Cannabinoid Mimetics", J Med Chem. (1995) 38(16):3094-3105.
El Nezhawy et al., "Synthesis and antioxidant activity of some thiazolidin-4-one derivatives", Springer; Chemical Monthly/Monatshefte für Chemie (2009) 140(5):531-539.
Endo et al., "Chemoselective Suzuki coupling of diborylmethane for facile synthesis of benzylboronates", Org Lett. (2011) 13(13):3368-3371.
Fan, et al. (2009): STN International HCAPLUS database, Columbus (OH), accession No. 2009: 425839; 6 pages.
Farquhar et al., "Intensely potent doxorubicin analogues: structure—activity relationship", J. Med. Chem. (1998) 41(6):965-972.
Ghosh et al., "Enantioselective total synthesis of (+)-largazole, a potent inhibitor of histone deacetylase", Org Lett. (2008) 10(17):3907-3909.

(56) References Cited

OTHER PUBLICATIONS

Giroux, A., "Synthesis of benzylic boronates via palladium-catalyzed cross-coupling reaction of bis(pinacolato)diboron with benzylic halides", Tetrahedron Lett. (2003) 44:233-235.
Gorovoy et al., "Boron-Containing Peptidomimetics—A Novel Class of Selective Anti-tubercular Drugs", Chem Biol Drug Des. (Jan. 2013) 81(3):408-413.
Gossinger et al., "Towards EPC-syntheses of the structural class of cochleamycins and macquarimicins. Part 3: EPC-syntheses of the beta-keto lactone subunits and first attempts towards the syntheses of the pentacyclic antibiotics of this group", Tetrahedron (2007) 63:8336-8350.
Graham et al., "D is for Drugs", Chemistry & Industry, Mar. 19, 2013, pp. 28-30, Downloaded from http://www.concertpharma.com/wp-content/uploads/2014/12/ChemistryIndustry-0313.pdf; 3 pages.
Greene, et al., "*Greene's Protective Groups in Organic Synthesis*", 4th Edition, (2007); pp. 774, 785 & 787.
Hall D.G., [Ed], Boronic Acids [vol. 2]: Preparations and applications in Organic Synthesis, Medicine and Materials, Wiley-VCH, Weinheim, $2^{nd}$ Edition (2011); TOC.
Hama et al., "Palladium-Catalyzed alpha-Arylation of Zinc Enolates of Esters: Reaction Conditions and Substrate Scope", J Org Chem. (2013) 78(17):8250-8266.
Hartung et al., "Highly Z-selective and Enantioselective Ring Opening/Cross Metathesis Catalyzed by Resolved Stereogenic-At-Ru Complex", J Am Chem Soc. (Jul. 2013) 135(28): 10183-10185.
Hecker et al., "Discovery of a Cyclic Boronic Acid beta-Lactamase Inhibitor (RPX7009) with Utility vs Class A Serine Carbapenemases", J Med Chem. (Mar. 2015) 58:3682-3692.
Hoveyda A., "Evolution of catalytic stereoselective olefin metathesis: From ancillary transformation to purveyor of stereochemical identity", J Org Chem. (Jun. 2014) 79(11): 4763-4792.
Imanishi et al., "Discovery of a Novel Series of Biphenyl Benzoic Acid Derivatives as Potent and Selective Human beta3-Adrenergic Receptor Agonists with Good Oral Bioavailability. Part I", J Med Chem. (2008) 51(6):1925-1944.
Inglis et al., "Observations on the Deprotection of Pinanediol and Pinacol Boronate Esters via Fluorinated Intermediates", J Org Chem. (2010) 75(2):468-471.
Ishii et al, "In vitro potentiation of carbapenems with ME1071, a Novel metallo-β-lactamase inhibitor, against metallo-β-lactamase producing pseudomonas aeruginosa clinical isolates." Antimicrob. Agents Chemother. doi:10.1128/AAC.01397-09 (2010) 54(9):3625-3629.
Ito et al., "An efficient constructive method for a tricyclic system: an important intermediate for the synthesis of tricycloclavulone", Tetrahedron Lett. (2003) 44:1259-1261.
Jadhav et al., "Direct synthesis of [alpha-[(tert-Butoxycarbonyl)amino]alkyl]- boronates from (alpha-Haloalkyl)boronates", Org Chem. (1996) 61(22):7951-7954.
Jagannathan et al., "Synthesis of Boronic Acid Analogues of alpha-Amino Acids by Introducing Side Chains as Electrophiles", J Org Chem. (2001) 66(19):6375-6380.
Jiang et al., "A Practical Synthesis of Cefcapene Pivoxil", Synthesis (2012) 44:207-214.
Johnson et al., "A drug targeting motif for glycosidase inhibitors: An iminosugar-boronate shows unexpectedly selective beta-galactosidase inhibition", Tetrahed Lttrs. (2002) 43(49):8905-8908.
Kabalka et al., "Synthesis of a series of bornonated unnatural cyclic amino acids as potential boron neutron capture therapy agents", Appl Organomet Chem. (2008) 22(9):516-522.
Kanai et al., "Synthesis of ortho-Acylbenzylboronates via Cross-Coupling Reaction of (Dialkoxyboryl)methylzinc Reagents with Haloarenes. A Stable ortho-Quinodimethane Precursor", Chem Letts. (1993) 22(5):845-848.
Kawamorita et al., "Synthesis of Primary and Secondary Alkylboronates through Site-Selective C(sp3)-H Activation with Silica-supported Monophosphine-Ir Catalysts", J Am Chem Soc. (2013) 135(8):2947-2950.

Kikuchi et al., "Comparison of the Pharmacodynamics of Biapenem in Bronchial Epithelial Lining Fluid in Healthy Volunteers Given Half-Hour and Three-Hour Intravenous Infusions", Antimicrob Agents Chemother. (Jul. 2009) 53(7):2799-2803.
Kint et al., "New-found fundamentals of bacterial persistence", Trends Microbiol. (2012) 20(12):577-585.
Kose et al., "Synthesis of photochromic 2,3-bis(5-methyl-2-phenyl-4-thiazolyl)-1,4-naphthoquinone derivatives", J Photochem Photobiol. A: Chemistry. (2011) 219(1):58-61.
Kotha et al., "Recent applications of the suzuki-miyaura cross-coupling reaction in organic synthesis", Tetrahedron (2002) 58:9633-9695.
Kumar et al., "Synthesis of intermediates for the lactone moiety of mevinic acids via tellurium chemistry", J. Org. Chem., (1994) 59(17):4760-4764.
Kumar et al., "Development of Practical Methodologies for the Synthesis of Functionalized Benzoboroxoles", Tetrahedron Lett. (Aug. 25, 2010) 51(34):4482-4485.
Kusakabe et al., "Preparation of Optically Acitve 2-Furylcarbinols by Kinetic Resolution Using the Sharpless Reagent and Their Application in Organic Synthesis", J org Chem (1989) 54(9):2085-2091.
Kuti et al., "Use of Monte Carlo simulation to design an optimized pharmacodynamic dosing strategy for meropenem", J Clin Pharmacol. (Oct. 2003) 43(10:1116-1123.
Laitar et al., "Catalytic diboration of aldehydes via insertion into the copper-boron bond", J Am Chem Soc. (2006) 128(34):11036-11037.
Lapuebla et al., "Activity of Meropenem Combined with RPX7009, a Novel beta-Lactamase Inhibitor, against Gram-Negative Clinical Isolates in New York City", Antimicrob Agents Chemother. (Aug. 2015) 59(8):4856-4860.
Larock R. [Ed.] *Comprehensive Organic Transformations*, VCH Publishers 1989; TOC, 11 pages.
Lee et al., "Vicinal Diboronates in High Enantiomeric Purity through Tandem Site-Selective NHC-Cu-Catalyzed Boron-Copper Additions to Terminal Alkynes", J Am Chem Soc. (Dec. 2009) 131(51):18234-18235.
Li et al, "Novel macrocyclic HCV NS3 protease inhibitors derived from α-amino cyclic boronates", Bioorganic Med Chem Lett. (2010) 20:5695-5700.
Li et al., "Synthesis and evaluation of novel alpha-amino cyclic boronates as inhibitors of HCV NS3 protease", Bioorg Med Chem Lett. (2010) 20:3550-3556.
Li et al., "Stereoselective total synthesis of etnangien and etnangien methyl ester", J Org Chem. (2010) 75(8):2429-2444.
Liang et al., "The Efficient Copper(I) (Hexabenzyl)tren Catalyst and Dendritic Analogues for Green "Click" Reactions between Azides and Alkynes in Organic Solvent and in Water: Positive Dendritic Effects and Monometallic Mechanism", Advance Syn Catal. (2011) 353(18): 3434-3450.
Lima et al., "Bioisosterism: A Useful Strategy for Molecular Modification and Drug Design", Curr Med Chem. (2005) 12:23-49.
Liu et al., "Selective Protein tyrosine phosphatase 1B inhibitors: Targeting the second phosphotyrosine binding site with non-carboxylic acid-containing ligands", J Med Chem. (2003) 46(16):3437-3440.
Liu et al., "Application of Stereoselective Ether Transfer to the Synthesis of Isotactic Polyethers", J Org Chem. (2010) 75(12):3953-3957.
Livermore et al., "Activities of NXL104 combinations with Ceftazidime and Aztreonam against Carbapenemase-producing Enterobacteriaceae", Antimicr Agents Chemother. (2011) 55(1):390-394.
Livermore et al., "Activity of biapenem (RPX2003) combined with the boronate beta-lactamase inhibitor RPX7009 against carbapenem-resistant Enterobacteriaceae", J Antimicrob Chemother. (Aug. 2013) 68(8):1825-1831.
Lodise et al., "Penetration of meropenem into epithelial lining fluid of patients with ventilator-associated pneumonia", Antimicrob Agents Chemother. (Apr. 2011) 55(4):1606-1610.
Malfertheiner et al., "Current concepts in the management of Helicobacter pylori infection: the Maastricht III Consensus Report", Gut (2007) 56(6):772-781.

(56) References Cited

OTHER PUBLICATIONS

Matteson et al., "Iodomethaneboronic Esters and Aminomethaneboronic Esters", J Organomet. Chem. (1979) 170:259-264.
Matteson et al., "A Directed Chiral Synthesis of Amino Acids from Boronic Esters", Tetrahedron Lett. (1987) 28(39):4499-4502.
Matteson, D.S., "Asymmetric Synthesis with Boronic Esters", Acc Chem Res. (1988) 21(8):294-300.
Matteson, "Boronic esters in stereodirected synthesis", Tetrahedron (1989) 45(7):1859-1885.
Matteson et al., "A stereospecific convergent coupling of nucleophilic and electrophilic chiral carbons", J. Am. Chem. Soc. (1989) 111:4399-4402.
Matteson et al., "Synthesis of asymmetrically deuterated glycerol and dibenzylglyceraldehyde via boronic esters", J. Am. Chem. Soc. (1990) 112:3964-3969.
Matteson et al., "(Alkoxyalkyl)boronic Ester Intermediates for Asymmetric Synthesis", Organometallics (1996) 15:152-163.
Matteson, "Alpha-Halo Baronic Esters in Asymmetric Synthesis", Tetrahedron (1998) 54(36):10555-10607.
Matteson et al., "Glass-Catalyzed Conversion of Boronic Esters of Asymmetric Diols to Diol Sulfites and Amine Complexes of Boron Halides", Oranometallics (2001) 20(13):2920-2923 & supporting Information (9 pages).
Matteson et al., "Cesium Alkyltrifluoroborates from Asymmetric Boronic Esters", Synlett (Jul. 2006) 20:3501-3503.
Matteson et al., "Synthesis of a (Beta-acetamido-alpha-acetoxyethyl) boronic ester via azido boronic esters", J Organomet Chem. (2008) 693:2258-2262.
Matteson, "Boronic Esters in Asymmetric Synthesis", J Org Chem. (Oct. 2013) 78(20): 10009-10023.
McOmie J.R.W. [Ed], *Protective Groups in Organic Chemistry*, Plenum Press, London & New York (1973); TOC, 3 pages.
Meanwell, "Synopsis of some recent tactical application of bioisosteres in drug design", J. Med. Chem. (2011) 54:2529-2591.
Mendoza et al., "Bis(phenylthio)methaneboronic Esters as Sources of Carbanions and Ketene Thioacetals", J Org Chem. (1979) 44(8):1352-1354.
Micalizio et al., "A Boronic Ester Annulation Strategy for Diversity-Oriented Organic Synthesis", Angew Chem Int Ed Engl. (2002) 41(1):152-154.
Montalbetti et al., "Amide bond formation and peptide coupling", Tetrahedron (2005) 61:10827-10852.
Montefour et al., "Acinetobacter baumannii: an emerging multidrug-resistant pathogen in critical care", Crit Care Nurse (2008) 28(1):15-25.
Morandi et al., "Structure-based optimization of cephalothin-analogue boronic acids as beta-lactamase inhibitors", Bioorg Med Chem. (2008) 16(3):1195-205. Epub Nov. 7, 2007.
Munar et al., "Drug Dosing Adjustments in Patients with Chronic Kidney Disease", Am Fam Physician (May 2007) 75(1): 1487-1496.
Nema et al., "Excipients and Their Role in Approved Injectable Products: Current Usage and Future Directions", PDA J Pharm Sci Technol. (2011) 65(3):287-332.
Ness et al., "Structure-based design guides the improved efficacy of deacylation transition state analogue inhibitors of Tem-1 beta-Lactamase", Biochemistry (2000) 39(18):5312-5321.
Nordmann et al., How to Detect NDM-1 Producers, J. Clin. Micro. (2011) 49:718-721.
Overman et al., "Organic Synthesis—Working with Hazardous Chemicals", Org Synth. (1990) 68: 182; 5 pages.
Panek et al., "Diastereoselectivity in the borane methyl sulfide promoted hydroboration of .alpha.-alkoxy-.beta, gamma.-unsaturated esters. Documentation of an alkoxy-directed hydroboration reaction", J. Org. Chem. (1992) 57(20):5288-5290.
Paquette L.A. [Ed.] *Encyclopedia of Reagents for Organic Synthesis*, vol. 1; J. Wiley & Sons (1995); Cover Only.
Patani et al., "Bioisosterism: A Rational Approach in Drug Design", Chem Rev. (1996) 96:3147-3176.
Paterson et al., "Extended-Spectrum beta-Lactamases: a Clinical Update", Clin Microbiol Rev. (2005) 18(4):657-686.
Perez et al., "Why are we afraid of Acinetobacter baumannii?", Expert Rev Anti Infect Ther. (2008) 6(3):269-71.
Pintaric et al., "An Opportunity for Mg-Catalyzed Grignard-Type Reactions: Direct Coupling of Benzylic Halides with Pinacolborane with 10 mol % of Magnesium", J Am Chem Soc. (2010) 132(34): 11825-11827.
Powell et al., "Compendium of excipients for parenteral formulations", PDA J Pharm Sci Technol. (1998) 52(5):238-311.
Reissig et al., "High diastereoselection in the alkylation of siloxy-substituted methyl cyclopropanecarboxylates: consequence of a pyramidal ester enolate anion?", J. Am. Chem. Soc. (1982) 104:1735-1737.
Robak et al., "Synthesis and applications of tert-butanesulfinamide", Chem Rev. (2010) 110(6):3600-3740.
Rodriguez-Martinez et al., "VIM-19, a Metallo-beta-lactamase with increased Carbapenemase Activity from *Escherichia coli* and Klebsiella pneumoniae", Antimicro Agents Chemother. (2010) 54(1):471-476.
Sabet et al., "In Vivo Efficacy of Carbavance (Meropenem/RPX7009) Against KPC-producing Enterobacteriaceae", Abstracts of the 54th Interscience Conference on Antimicrobial Agents and Chemotherapy (Sep. 5-9, 2014) F-958; 3 pages.
Sawant et al., "Synthesis of the C1-C13 Fragment of Biselyngbyaside", Synlett (2011) 20: 3002-3004.
Sawyer et al., "Physical properties and synthetic utility of a-alkoxyorganolithium species as studied through ligand selectivity in tin-lithium exchange", J. Am. Chem. Soc. (1988) 110:842-853.
Selander et al., "Palladium-catalyzed allylic C—OH functionalization for efficient synthesis of functionalized allylsilanes", J Am Chem Soc. (2011) 133(3):409-411.
Shaffer, Robyn Kroop, "The Challenge of Antibiotic-Resistant *Staphylococcus*: Lessons from Hospital Nurseries in the mid-20th Century", Yale J Biol Med. (2013) 86:261-270.
Shao et al., "Asymmetric hydrogenation of 3,5-Dioxoesters catalyzed by Ru-binap complex: A short step asymmetric synthesis of 6-substituted 5,6-dehydro-2-pyrones", Tetrahedron (1993) 49(10):1997-2010.
Singer et al., "Catalytic, enantioselective acetate aldol additions to alpha-, beta-ynals: Preparation of optically active propargylic alcohols", Tetrahedron (1998) 54(25): 7025-7032.
Singh et al., "Asymmetric Homologation of Boronic Esters Bearing Azido and Silyloxy Substituents", J Org Chem. (2000) 65(20):6650-6653 and Erratum: J Org Chem. (2001) 66(22):7560.
Sliwka et al., "Synthetic Sulfur Carotenoids II: Optically Active Carotenoid Thiols", Tetrahedron: Asymmetry (1993) 4(3):361-368.
Solladié et al., "First Stereocontrolled Synthesis of the (3S,5R,7R,10R,11R)-C1-C13 Fragment of Nystatin A(1)", J Org Chem. (1999) 64(15):5447-5452.
Souto et al., "Synthesis and biological characterization of the histone deacetylase inhibitor largazole and c7-modified analogues", J. Med. Chem. (2010) 53(12):4654-4667.
Spiegel et al., "CP-263,114 synthetic studies. Construction of an isotwistane ring system via rhodium carbenoid C—H insertion", Tetrahedron (2002) 58:6545-6554.
Sun et al., "Programmed Synthesis of a Contiguous Stereotriad Motif by Triple Stereospecific Reagent-controlled Homologation", Org Lttr. (Jul. 2013) 15(17):4500-4503.
Teo et al., "Efficient and highly aldehyde selective Wacker oxidation", Org Lett. (2012) 14(13):3237-3239.
Theuretzbacher et al., "Update on antibacterial and antifungal drugs—can we master the resistance crisis?", Curr Opin Pharmacol. (2011) 11:429-432.
Vasil'Ev et al., (1977): STN International HCAPLUS database, Columbus (OH), accession No. 1977: 72730; 1 page.
Vitor et al., "Rhenium(I)- and technetium(I) tricarbonyl complexes anchored by bifunctional pyrazole-diamine and pyrazole-dithioether chelators", J Organometal Chem (2004) 689(25):4764-4774.
Waley, Stephen G., "A quick method for the determination of inhibition constants", Biochem J. (1982) 205(3):631-633.
Walsh et al., "Metallo-beta-Lactamases: the Quiet before the Storm?", Clin Microbiol Rev. (2005) 18(2):306-325.
Wang et al., "Recognition and resistance in TEM beta-lactamase", Biochemistry (2003) 42(28):8434-8444.

(56) References Cited

OTHER PUBLICATIONS

Webb et al., "Metal catalysed hydroboration of vinyl sulfides, sulfoxides, sulfones, and sulfonates", J Mol Cat A: Chem. (2007) 275:91-100.

Wohlrab et al., "Total synthesis of plusbacin A3: a depsipeptide antibiotic active against vancomycin-resistant bacteria", J. Am. Chem. Soc. (2007) 129:4175-4177.

Xia et al., "Synthesis and SAR of novel benzoxaboroles as a new class of beta-lactamase inhibitors", Bioorg Med Chem Lett. (2011) 21:2533-2536.

Xie et al., "Group-assisted purification (GAP) chemistry for the synthesis of Velcade via asymmetric borylation of N-phosphinylimines", Beilstein J Org Chem (Mar. 2014) 10:746-751.

Yamamoto et al., "Iridium-catalyzed hydroboration of alkenes with pinacolborane", Tetrahedron (2004) 60:10695-10700.

Yanagisawa et al., "Nonpeptide angiotensin II receptor antagonists: synthesis, biological activities, and structure-activity relationships of imidazole-5-carboxylic acids bearing alkyl, alkenyl, and hydroxyalkyl substituents at the 4-position and their related compounds", J Med Chem. (1996) 39(1):323-338.

Yuen et al., "Deprotection of pinacolyl boronate esters via hydrolysis of intermediate potassium trifluoroborates", Tetrahed Lttr. (2005)46(46):7899-7903.

International Search Report and Written Opinion dated Feb. 1, 2016 for International Application No. PCT/US2015/060556, filed Nov. 13, 2015.

International Preliminary Report of Patentability dated May 23, 2017 for International Application No. PCT/US2015/060556, filed Nov. 13, 2015.

CYCLIC BORONIC ACID ESTER DERIVATIVES AND THERAPEUTIC USES THEREOF

CROSS-REFERENCE TO RELATED APPLICATIONS

This application is a 371 of International Application No. PCT/US2015/060556, filed Nov. 13, 2015, which claims priority to and the benefit of U.S. Provisional Application 62/081,136 filed Nov. 18, 2014, the entire contents of all of which are incorporated herein by reference.

BACKGROUND

Field of the Invention

The present invention relates to the fields of chemistry and medicine. More particularly, the present invention relates to boronic acid compounds, compositions, their preparation, and their use as therapeutic agents.

Description of the Related Art

Antibiotics have been effective tools in the treatment of infectious diseases during the last half-century. From the development of antibiotic therapy to the late 1980s, developed countries possessed almost complete control over bacterial infections. However, in response to the pressure of antibiotic usage, multiple resistance mechanisms have become widespread and are threatening the clinical utility of anti-bacterial therapy. The increase in antibiotic resistant strains has been particularly common in major hospitals and care centers. Consequently, these institutions have experienced increased morbidity and mortality, longer patient hospitalization, and higher treatment costs.

Various bacterial species have evolved β-lactam deactivating enzymes, namely, β-lactamases, that counter the efficacy of the various β-lactam antibiotics. β-lactamases can be grouped into 4 classes based on their amino acid sequences, namely, Ambler classes A, B, C, and D. Enzymes in classes A, C, and D include active-site serine β-lactamases while class B enzymes, which are encountered less frequently, are Zn-dependent. These enzymes catalyze the chemical degradation of β-lactam antibiotics, rendering them inactive. Some β-lactamases can be transferred within and between various bacterial strains and species. The rapid spread of bacterial resistance and the evolution of multi-resistant strains severely limit β-lactam treatment options available.

The increase of class D β-lactamase-expressing bacterium strains such as *Acinetobacter baumannii* has become an emerging multidrug-resistant threat. *A. baumannii* strains express A, C, and D class β-lactamases. The class D β-lactamases such as the OXA families are particularly effective at destroying carbapenem type f-lactam antibiotics, e.g., imipenem, the active carbapenems component of Merck's Primaxin® (Montefour, K.; et al. Crit. Care Nurse 2008, 28, 15; Perez, F. et al. Expert Rev. Anti Infect. Ther. 2008, 6, 269; Bou, G.; Martinez-Beltran, J. Antimicrob. Agents Chemother. 2000, 40, 428. 2006, 50, 2280; Bou, G. et al, J. Antimicrob. Agents Chemother. 2000, 44, 1556). This has imposed a pressing threat to the effective use of drugs in that category to treat and prevent bacterial infections. Indeed the number of catalogued serine-based β-lactamases has exploded from less than ten in the 1970s to over 300 variants. These issues fostered the development of five "generations" of cephalosporins. When initially released into clinical practice, extended-spectrum cephalosporins resisted hydrolysis by the prevalent class A β-lactamases, TEM-1 and SHV-1. However, the development of resistant strains by the evolution of single amino acid substitutions in TEM-1 and SHV-1 resulted in the emergence of the extended-spectrum β-lactamase (ESBL) phenotype.

New β-lactamases have recently evolved that hydrolyze the carbapenem class of antimicrobials, including imipenem, biapenem, doripenem, meropenem, and ertapenem, as well as other β-lactam antibiotics. These carbapenemases belong to molecular classes A, B, and D. Class A carbapenemases of the KPC-type predominantly in *Klebsiella pneumoniae* but now also reported in other Enterobacteriaceae, *Pseudomonas aeruginosa* and *Acinetobacter baumannii*. The KPC carbapenemase was first described in 1996 in North Carolina, but since then has disseminated widely in the US. It has been particularly problematic in the New York City area, where several reports of spread within major hospitals and patient morbidity have been reported. These enzymes have also been recently reported in France, Greece, Sweden, United Kingdom, and an outbreak in Germany has recently been reported. Treatment of resistant strains with carbapenems can be associated with poor outcomes.

Another mechanism of β-lactamase mediated resistance to carbapenems involves combination of permeability or efflux mechanisms combined with hyper production of beta-lactamases. One example is the loss of a porin combined in hyperproduction of ampC beta-lactamase results in resistance to imipenem in *Pseudomonas aeruginosa*. Efflux pump over expression combined with hyperproduction of the ampC β-lactamase can also result in resistance to a carbapenem such as meropenem.

Due to these problems associated with β-lactamase mediated resistance, there is a need for improved β-lactamase inhibitors.

SUMMARY OF THE INVENTION

The present invention relates to antimicrobial agents and potentiators thereof. Some embodiments include compounds, compositions, pharmaceutical compositions, use and preparation thereof. In, particular, some embodiments, relate to cyclic boronic acid ester derivatives.

Some embodiments disclosed herein include a compound having the structure of formula Ia or formula Ib:

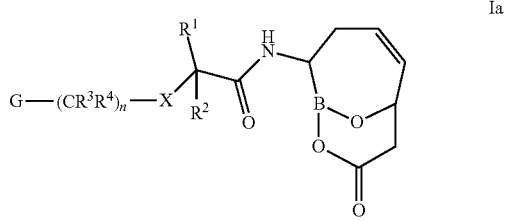

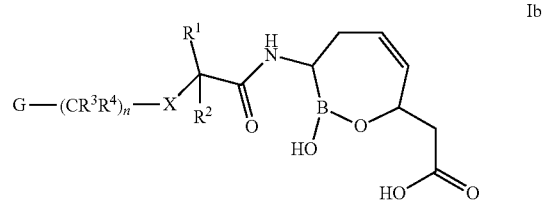

or a pharmaceutically acceptable salt thereof, wherein:

$R^1$ and $R^2$ can be independently selected —H, —OH, halo, optionally substituted $C_{1-10}$ alkoxy, optionally substituted $C_{1-10}$ alkyl, optionally substituted $C_{2-10}$ alkenyl, optionally substituted $C_{2-10}$ alkynyl, optionally substituted $C_{3-7}$ carbocyclyl, optionally substituted 3-8 membered heterocyclyl, optionally substituted $C_{6-10}$ aryl, and optionally substituted 5-10 membered heteroaryl, or alternatively $R^1$ and $R^2$ are taken together with the carbon atom to which they are attached to form an optionally substituted $C_{3-6}$ carbocyclyl or an optionally substituted 3-6 membered heterocyclyl;

each $R^3$ and $R^4$ can be independently selected from —H, —OH, halo, optionally substituted $C_{1-10}$ alkoxy, optionally substituted $C_{1-10}$ alkyl, optionally substituted $C_{2-10}$ alkenyl, optionally substituted $C_{2-10}$ alkynyl, optionally substituted $C_{3-7}$ carbocyclyl, optionally substituted 3-8 membered heterocyclyl, optionally substituted $C_{6-10}$ aryl, and optionally substituted 5-10 membered heteroaryl, or alternatively $R^3$ and $R^4$ in each $CR^3R^4$ unit are taken together with the atoms to which they are attached to form an optionally substituted $C_{3-6}$ carbocyclyl or an optionally substituted 3-6 membered heterocyclyl;

X can be selected from —S—, —S(O)—, —S(O)$_2$—, —O—, and —NR$^7$—;

G can be selected from —NR$^7$R$^8$, —N$_3$, —C(O)NR$^7$R$^8$, —S(O)$_2$NR$^7$R$^8$, —SR$^9$, —OR$^9$, CH$_2$NR$^7$C(O)R$^{10}$, —C(=NOR$^9$)—Z, —C(O)OR$^9$, —C(O)NR$^7$(OR$^9$), —NR$^7$(OR$^9$), —NR$^7$C(O)R$^{10}$, —NR$^7$C(O)NR$^8$R$^{7a}$, —NR$^7$C(O)OR$^9$, —NR$^7$S(O)$_2$R$^9$, —NR$^7$S(O)$_2$NR$^8$R$^{7a}$, —NR$^7$NR$^8$R$^{7a}$, C(O)NR$^7$NR$^8$R$^{7a}$, —S(O)$_2$NR$^7$NR$^8$R$^{7a}$, —C(=NR$^7$)R$^8$, —C(=NR$^7$)NR$^8$R$^{7a}$, —NR$^7$CR$^{10}$(=NR$^8$), —NR$^7$C(=NR$^8$)NR$^{7a}$R$^{8a}$, —CN, $C_{1-10}$ alkyl optionally substituted with one or more $R^{11}$, $C_{2-10}$ alkenyl optionally substituted with one or more $R^{11}$, $C_{2-10}$ alkynyl optionally substituted with one or more $R^{11}$, $C_{3-7}$ carbocyclyl optionally substituted with one or more $R^{11}$, 5-10 membered heterocyclyl optionally substituted with one or more $R^{11}$, $C_{6-10}$ aryl optionally substituted with one or more $R^{11}$, 5-10 membered heteroaryl optionally substituted with one or more $R^{11}$, $C_{3-7}$ carbocyclyl-$C_{1-6}$ alkyl optionally substituted with one or more $R^{11}$, 5-10 membered heterocyclyl-$C_{1-6}$ alkyl optionally substituted with one or more $R^{11}$, $C_{6-10}$ aryl-$C_{1-6}$ alkyl optionally substituted with one or more $R^{11}$, and 5-10 membered heteroaryl-$C_{1-6}$ alkyl optionally substituted with one or more $R^{11}$;

$R^7$, $R^{7a}$, $R^8$, and $R^{8a}$ can be independently selected from H, —$C_{1-9}$ alkyl, —$C_{1-9}$ alkylR$^{10}$, —OR$^9$, —CH(=NH), optionally substituted $C_{6-10}$ aryl, optionally substituted 5-10 membered heteroaryl, optionally substituted $C_{3-10}$ carbocyclyl, and optionally substituted 3-10 membered heterocyclyl;

each $R^9$ can be independently selected from H, $C_{1-9}$ alkyl, $C_{1-9}$ alkylR$^{10}$, optionally substituted $C_{6-10}$ aryl, optionally substituted 5-10 membered heteroaryl, optionally substituted $C_{3-10}$ carbocyclyl, and optionally substituted 3-10 membered heterocyclyl;

each $R^{10}$ can be independently selected from optionally substituted $C_{6-10}$ aryl, optionally substituted 5-10 membered heteroaryl, optionally substituted $C_{3-10}$ carbocyclyl, and optionally substituted 3-10 membered heterocyclyl;

$R^{11}$ can be selected from $C_{1-4}$ alkyl, —OR$^9$, —$C_{1-6}$ alkyl-COOR$^9$, optionally substituted $C_{6-10}$ aryl, optionally substituted 5-10 membered heteroaryl, optionally substituted $C_{3-10}$ carbocyclyl, and optionally substituted 3-10 membered heterocyclyl, —SR$^9$, —NR$^7$R$^8$, halo, —CN, —C(O)N$^R$7R$^8$, and —NR$^7$C(O)R$^{10}$;

Z can be selected from optionally substituted $C_{6-10}$ aryl, optionally substituted $C_{3-10}$ carbocyclyl, optionally substituted 5-10 membered heteroaryl, optionally substituted 3-10 membered heterocyclyl, —CH$_2$Y, —CH(Y)$_2$, and —C(Y)$_3$;

Y can be selected from halo, cyano, and azido;

n can be an integer selected from 0, 1, and 2.

Some embodiments include a pharmaceutical composition comprising a therapeutically effective amount of a compound disclosed herein and a pharmaceutically acceptable excipient.

Some embodiments include a method of treating a bacterial infection, comprising administering to a subject in need thereof a compound disclosed herein.

DETAILED DESCRIPTION

The present invention relates to antimicrobial agents and potentiators thereof. Some embodiments include compounds, compositions, pharmaceutical compositions, uses thereof, including methods of preparation and methods of treatment. In particular, the present invention relates to cyclic boronic acid ester derivatives. In some embodiments, the cyclic boronic acid ester derivatives have the structure of formula Ia or Ib as described above.

Some embodiments of the compound of formula Ia or Ib have the defined stereochemistry of the structure of formula IIa or IIb:

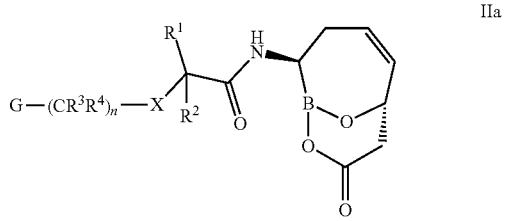

IIa

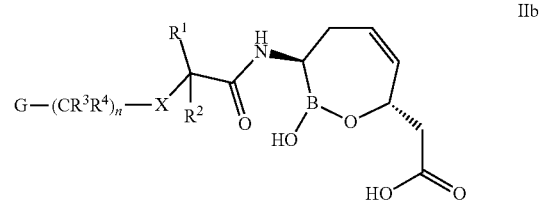

IIb or a pharmaceutically acceptable salt thereof.

In some embodiments of the compound of formulas Ia, Ib, IIa, and IIb, X is —S—.

In some embodiments of the compound of formulas Ia, Ib, IIa, and IIb, G is a heteroaryl optionally substituted with one or more $R^{11}$.

In some embodiments of the compound of formulas Ia, Ib, IIa, and IIb, G is selected from the group consisting of $C_{1-4}$ alkyl, phenyl, imidazoyl, pyrazoyl, triazolyl, tetrazolyl, thiazolyl, thiadiazolyl, oxazolyl, oxadiazolyl, isoxazolyl, isothiazolyl, pyridinyl, pyrazinyl, pyrimidinyl, pyridazinyl, azetidinyl, and pyrazinyl, each optionally substituted by one or two $R^{11}$.

In some embodiments of the compound of formulas Ia, Ib, IIa, and IIb, G is —CH$_3$.

In some embodiments of the compound of formulas Ia, Ib, IIa, and IIb, G is —CN.

In some embodiments of the compound of formulas Ia, Ib, IIa, and IIb, G is —CHF$_2$.

In some embodiments of the compound of formulas Ia, Ib, IIa, and IIb, G is tetrazolyl optionally substituted with one or more R$^{11}$.

In some embodiments of the compound of formulas Ia, Ib, IIa, and IIb, G is 1-methyl tetrazolyl.

In some embodiments of the compound of formulas Ia, Ib, IIa, and IIb, G is triazolyl optionally substituted with one or more R$^{11}$.

In some embodiments of the compound of formulas Ia, Ib, IIa, and IIb, G is 4-methyl triazolyl.

In some embodiments of the compound of formulas Ia, Ib, IIa, and IIb, G is thiadiazolyl optionally substituted with one or more R$^{11}$.

In some embodiments of the compound of formulas Ia, Ib, IIa, and IIb, G is 5-amino-1,3,4-thiadiazolyl.

In some embodiments of the compound of formulas Ia, Ib, IIa, and IIb, G is 5-methyl-1,3,4-thiadiazolyl.

In some embodiments of the compound of formulas Ia, Ib, IIa, and IIb, each R$^1$, R$^2$, R$^3$, and R$^4$ can be independently selected from —H, —OH, halo, optionally substituted C$_{1-10}$ alkoxy, optionally substituted C$_{1-10}$ alkyl, optionally substituted C$_{2-10}$ alkenyl, optionally substituted C$_{2-10}$ alkynyl, optionally substituted C$_{3-7}$ carbocyclyl, optionally substituted 3-8 membered heterocyclyl, optionally substituted C$_{6-10}$ aryl, and optionally substituted 5-10 membered heteroaryl.

In some embodiments of the compound of formulas Ia, Ib, IIa, and IIb, R$^1$ is H.

In some embodiments of the compound of formulas Ia, Ib, IIa, and IIb, R$^2$ is H.

In some embodiments of the compound of formulas Ia, Ib, IIa, and IIb, R$^3$ is H.

In some embodiments of the compound of formulas Ia, Ib, IIa, and IIb, R$^4$ is H.

In some embodiments of the compound of formulas Ia, Ib, IIa, and IIb, n is 0.

In some embodiments of the compound of formulas Ia, Ib, IIa, and IIb, n is 1.

In some embodiments of the compound of formulas Ia, Ib, IIa, and IIb, each R$^1$, R$^2$, R$^3$ and R$^4$ are H and n is 1.

Some embodiments include a compound selected from the group consisting of:

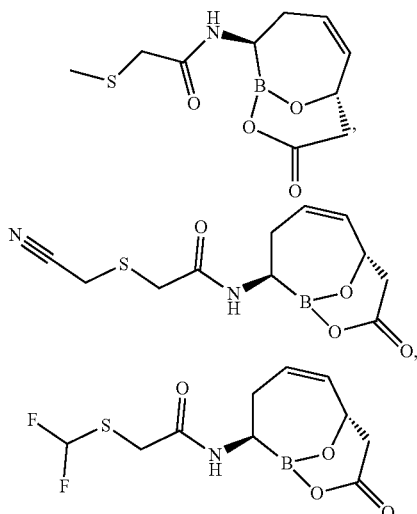

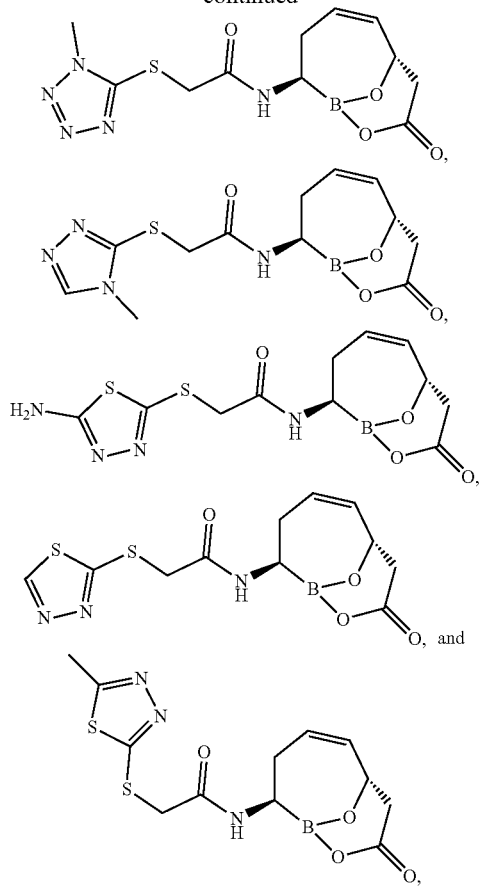

or a pharmaceutically acceptable salt thereof.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

"Solvate" refers to the compound formed by the interaction of a solvent and a compound described herein or salt thereof. Suitable solvates are pharmaceutically acceptable solvates including hydrates.

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable salts can also be formed using inorganic and organic bases. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_a$-b" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—$CH_3CH_2CH_2CH_2$—, $CH_3CH_2CH(CH_3)$—, $(CH_3)_2CHCH_2$—, and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, isobutyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-sulfonamido" group refers to a "—N(R$_A$)SO$_2$R$_B$" group in which R$_A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-carbamyl" group refers to an "—N(R$_A$)C(=O)OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-thiocarbamyl" group refers to an "—N(R$_A$)C(=S)OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes free amino (i.e., —$NH_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Unless otherwise indicated, wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

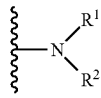

and $R^1$ and $R^2$ are defined as selected from the group consisting of hydrogen and alkyl, or $R^1$ and $R^2$ together with the nitrogen to which they are attached form a heteroaryl, it is meant that $R^1$ and $R^2$ can be selected from hydrogen or alkyl, or alternatively, the substructure has structure:

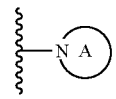

where ring A is a heteroaryl ring containing the depicted nitrogen.

Similarly, when two "adjacent" R groups are said to form a ring "together with the atoms to which they are attached," it is meant that the collective unit of the atoms, intervening bonds, and the two R groups are the recited ring. For example, when the following substructure is present:

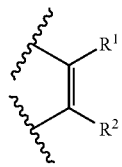

and $R^1$ and $R^2$ are defined as selected from the group consisting of hydrogen and alkyl, or $R^1$ and $R^2$ together with the atoms to which they are attached form an aryl or carbocylyl, it is meant that $R^1$ and $R^2$ can be selected from hydrogen or alkyl, or alternatively, the substructure has structure:

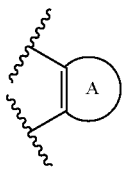

where A is an aryl ring or a carbocylyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

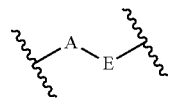

includes the substituent being oriented such that the A is attached at the leftmost attachment point of the molecule as well as the case in which A is attached at the rightmost attachment point of the molecule.

As used herein, "isosteres" of a chemical group are other chemical groups that exhibit the same or similar properties. For example, tetrazole is an isostere of carboxylic acid because it mimics the properties of carboxylic acid even though they both have very different molecular formulae. Tetrazole is one of many possible isosteric replacements for carboxylic acid. Other carboxylic acid isosteres contemplated include —$SO_3H$, —$SO_2HNR$, —$PO_2(R)_2$, —$PO_3(R)_2$, —$CONHNHSO_2R$, —$COHNSO_2R$, and —CONRCN, where R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. In addition, carboxylic acid isosteres can include 5-7 membered carbocycles or heterocycles containing any combination of $CH_2$, O, S, or N in any chemically stable oxidation state, where any of the atoms of said ring structure are optionally substituted in one or more positions. The following structures are non-limiting examples of carbocyclic and heterocyclic isosteres contemplated. The atoms of said ring structure may be optionally substituted at one or more positions with R as defined above.

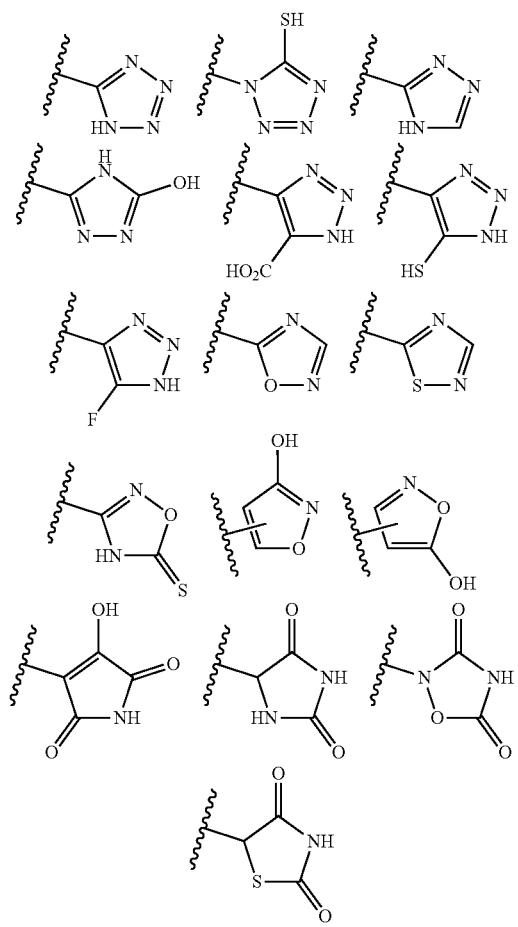

It is also contemplated that when chemical substituents are added to a carboxylic isostere, the compound retains the properties of a carboxylic isostere. It is contemplated that when a carboxylic isostere is optionally substituted with one or more moieties selected from R as defined above, then the substitution and substitution position is selected such that it does not eliminate the carboxylic acid isosteric properties of the compound. Similarly, it is also contemplated that the placement of one or more R substituents upon a carbocyclic or heterocyclic carboxylic acid isostere is not a substitution at one or more atom(s) that maintain(s) or is/are integral to the carboxylic acid isosteric properties of the compound, if such substituent(s) would destroy the carboxylic acid isosteric properties of the compound.

Other carboxylic acid isosteres not specifically exemplified in this specification are also contemplated.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice guinea pigs, or the like.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

Methods of Preparation

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Synthesis of Compounds of Formula I

The following example schemes are provided for the guidance of the reader, and collectively represent an example method for making the compounds encompassed herein. Furthermore, other methods for preparing compounds described herein will be readily apparent to the person of ordinary skill in the art in light of the following reaction schemes and examples. Unless otherwise indicated, all variables are as defined above.

Compounds of formula IIa can be prepared as depicted in scheme 1 from key intermediates of formula XI, which may be assembled by known reactions (Boronic Acids: Preparations and Applications in Organic Synthesis, Medicine and Materials, D. G. Hall, ed., Wiley-VCH, Weinheim, 2011, which is incorporated by reference herein in its entirety).

Scheme 1
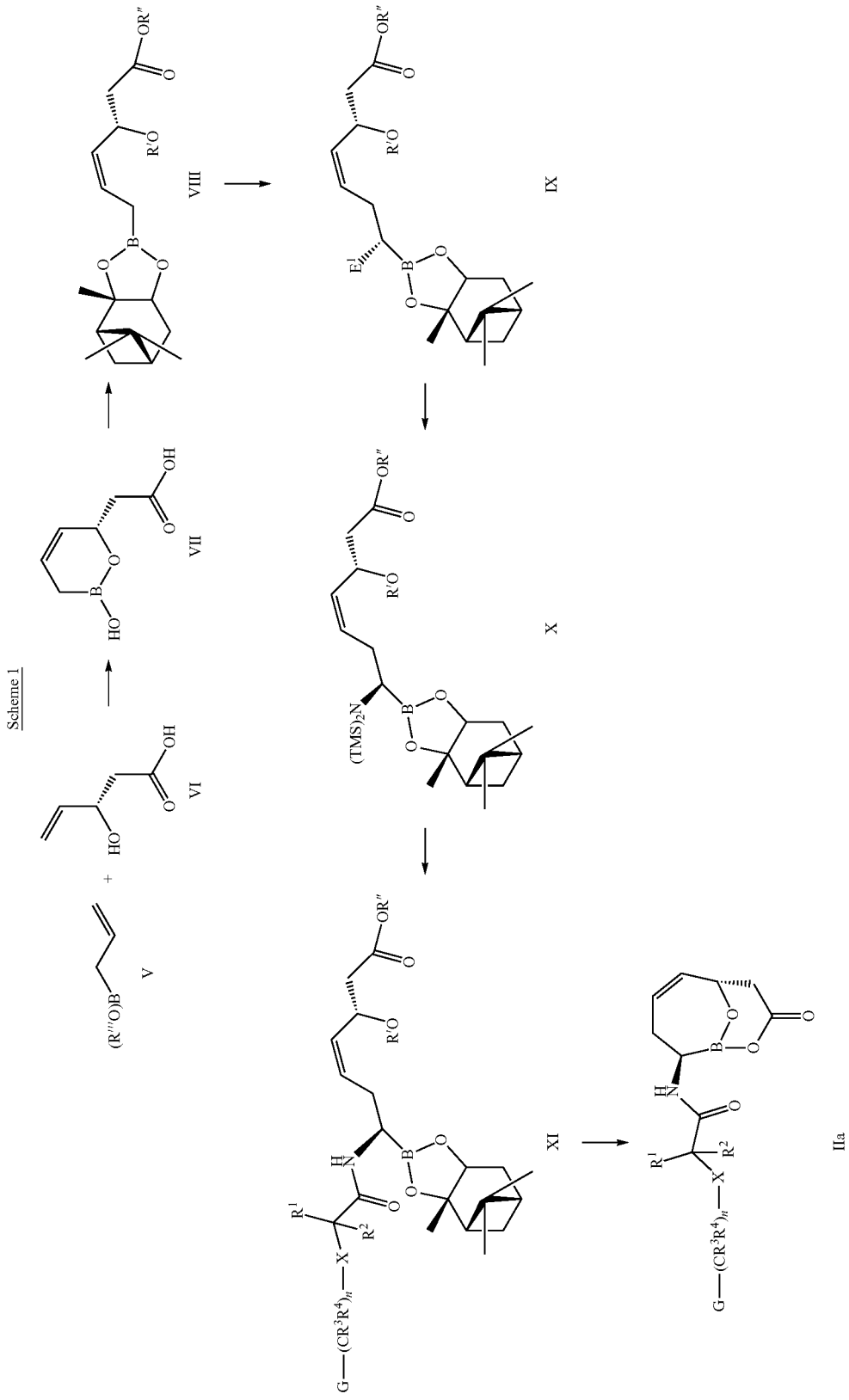

Allylboronate esters where R''' is $C_{1-4}$ acyclic alkyl group undergo reaction with allylic alcohols of formula VI (*J. Med. Chem.*, 2010, 53, 4654-4667) in intermolecular transesterification. Such hemiboronates upon cyclization when treated under ring closing metathesis (RCM) conditions give compounds of formula VII (*Angew. Chem. Int. Ed. Engl.*, 2002, 41, 152-4). The references for these two reaction steps are incorporated by reference herein in their entirety. Enantiomerically pure secondary alcohols of formula VI may be made from known conditions including but not limited to enzymatic resolutions. The cyclic hemiboronates of formula VII react with chiral auxiliary of desired stereochemistry to give an acyclic boronate intermediate. Enantiomerically pure pinanediol upon reaction with compounds of formula VII result in ring opened Matteson precursor of formula VIII. Such compounds of formula VIII may be achieved by means of several earlier known methods (WO00458679) with conventional protecting groups, such as those described in *Protective Groups in Organic Chemistry* (ed. J. F. W. McOmie, Plenum, 1973); and *Protecting Groups in Organic Synthesis* (P. G. M. Wutts, T. W. Green, Wiley, New York, 1999). These three references are incorporated by reference herein in their entirety. Compounds of formula VIII undergo homologation by halomethylene insertion in a highly enantioselective Matteson reaction (*J. Org. Chem.*, 2013, 78, 10009-10023, which is incorporated herein by reference in its entirety) to give IX. Such key intermediates of formula IX where $E^1$=Cl and R' and R'' are H may be prepared by earlier described methods (WO09064414, WO10130708, both of which are incorporated by reference herein in their entirety). In an alternate sequence, compounds of formula IX where $E^1$=Cl and R' is TBS and R'' is t-Butyl or R' and R'' are protected together as isopropylidine or any other groups protected separately or together in cyclic form may be made from compounds of formula VIII via homologation to yield a chloromethylene addition product with good stereocontrol by Matteson reaction conditions (WO0946098). Compounds of formula IX where $E^1$ is bromo may be made analogously to the chloro compounds, utilizing dibromomethane (*J. Am. Chem. Soc.* 1990, 112, 3964-969, incorporated by reference herein in its entirety). The halo derivatives of formula IX where $E^1$ is Cl or Br undergo stereospecific substitution to form amides in a two-step sequence by HMDS displacement followed by amide formation (*J. Organomet. Chem.* 1979, 170, 259-64, incorporated by reference herein in its entirety) to give compounds of formula XI.

Simultaneous deprotection of pinane ester and alcohol and acid protective groups of compounds of formula XI can be achieved by heating with aq trifluoroacetic acid or dilute HCl, affording the desired compounds of structure I. This transformation may also be achieved by treatment with $BCl_3$ or $BBr_3$ (WO09064414, incorporated by reference herein in its entirety). Alternatively, the deprotection may be attained via trans-esterification with isobutyl boronic acid in presence of dilute acid (WO09064413, incorporated by reference herein in its entirety) or via other known methods (*J. Org. Chem.* (2010), 75, 468-471, incorporated by reference herein in its entirety).

Intermediates of formula XI or XV may be also prepared following the sequence described in scheme 2 via asymmetric borylation of N-tert-butanesulfinyl imines with bis(pinacolato)diboron (*J. Org. Chem.*, 2014, 79, 3671-3677, incorporated by reference herein in its entirety). Precursors of formula XIV can be prepared from convergent or linear approaches as shown below.

Intermediates of formula XI or XV may be also prepared following the sequence described in scheme 2 via asymmetric borylation of N-tert-butanesulfinyl imines with bis(pinacolato)diboron (*J. Org. Chem.*, 2014, 79, 3671-3677). Precursors of formula XIV can be prepared from convergent or linear approaches as shown below.

Scheme 2

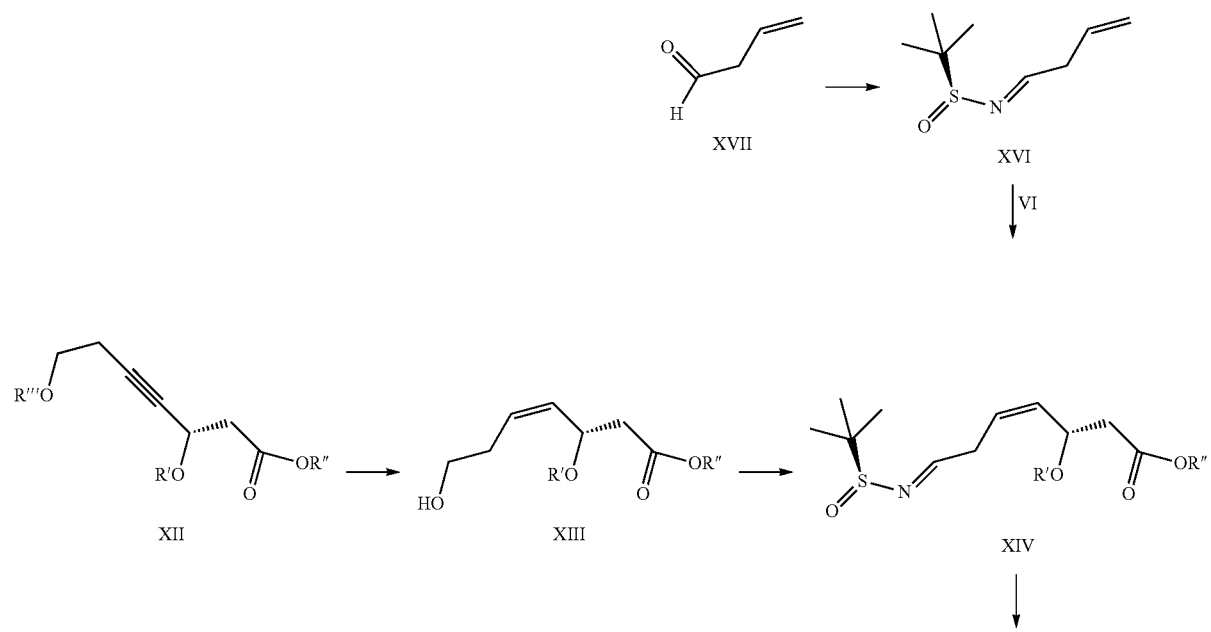

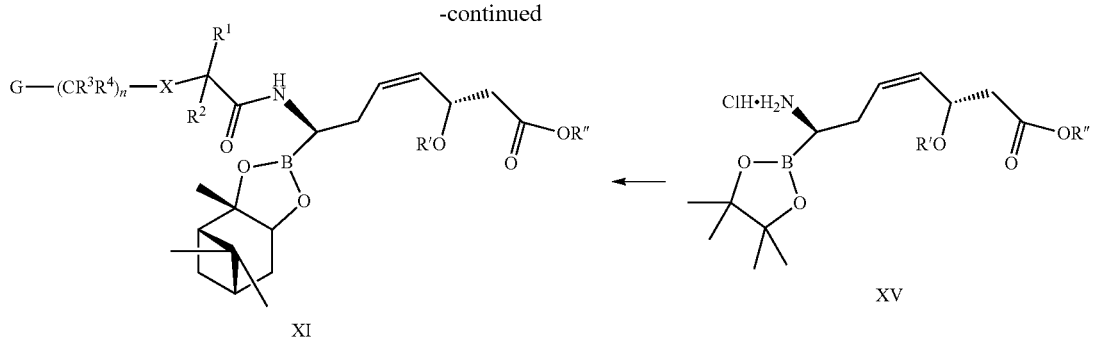

XI

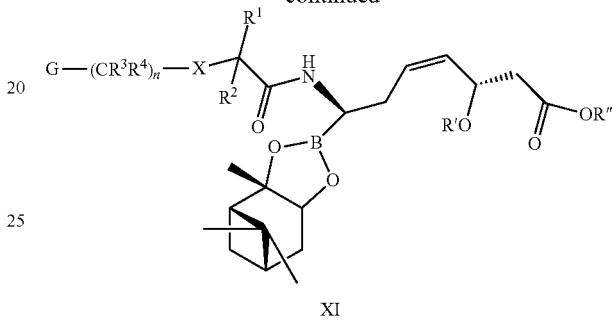

XV

A catalytic, enantioselective acetate-aldol addition reaction of silyl ketene acetals with α,β-ynals in presence of a chiral Ti(IV) complex provides access to optically active β-hydroxy-γ-alkynyl esters (XII) in high enantiomeric excess. (*Tetrahedron* 1998, 54, 7025-7032, incorporated by reference herein in its entirety). Such intermediates of XII undergo selective cis-hydrogenation (*Org. Synth.* 1990, 68, 182, incorporated by reference herein in its entirety) followed by deprotection to give XIII. Ellman precursor containing chiral tert-butanesutfinamide (XIV) are readily made by oxidation of intermediates of formula XIII and condensation of sulfonyl amide. In an alternate approach, XIV may be also prepared by cis-selective olefin metathesis of XVI and VI to result in corresponding product with high Z-selectivity in presence of an appropriate catalyst (*J. Am. Chem. Soc.* 2013, 135, 10183, incorporated by reference herein in its entirety). Intermediates of XV may be directly used from corresponding amide formation or converted to amide after conversion to a more stable pinnae diol ester to XI.

Intermediate of formula XI can also be made via a Z-selective metathesis (*J. Org. Chem.*, 2014, 79, 4763-4792, incorporated by reference herein in its entirety) from a hemoallylic boronate (XIX) and protected secondary alcohol of formula VI. Intermediate XIX can be made from the pinanediol ester of allylic boronate via Matteson reaction followed by amide formation as described above.

Scheme 3

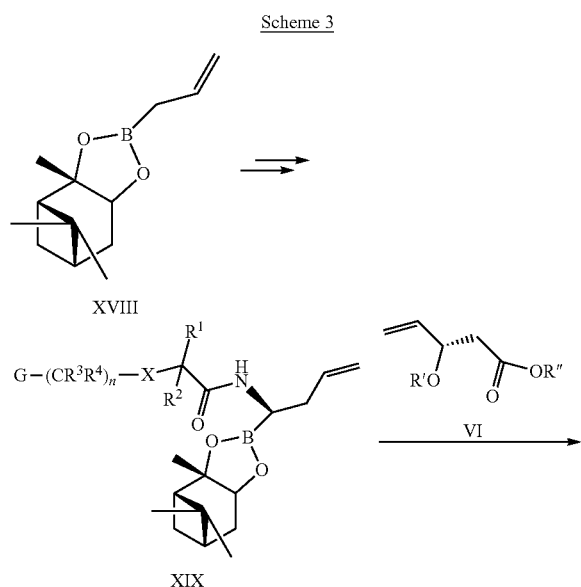

Compounds of free carboxylic acid salts (IIb) as shown in scheme 4 may be synthesized via hydrolysis from compounds of formula IIa. The bridged prodrug (IIa) upon the treatment of aqueous bases in organic medium readily undergo in the ring opening to form corresponding carboxylic acid salt. The monovalent cations such as sodium or potassium may be attained by the choice of the bases used in the transformation. Organic bases also may be used in such conversions to give corresponding salts of IIb.

Scheme 4

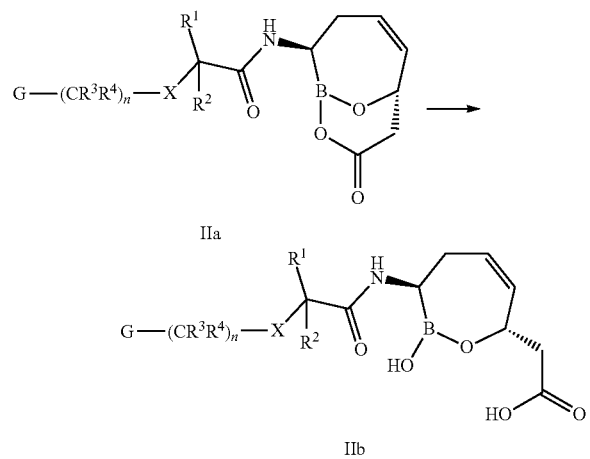

Administration and Pharmaceutical Compositions

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated herein by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such as sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (e.g. drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

Ophthalmically acceptable antioxidants include, but are not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan. In some embodiments, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day.

Methods of Treatment

Some embodiments of the present invention include methods of treating bacterial infections with the compounds and compositions comprising the compounds described herein. Some methods include administering a compound, composition, pharmaceutical composition described herein to a subject in need thereof. In some embodiments, a subject can be an animal, e.g., a mammal, a human. In some embodiments, the bacterial infection comprises a bacterial species described herein. As will be appreciated from the foregoing, methods of treating a bacterial infection include methods for preventing bacterial infection in a subject at risk thereof.

In some embodiments, the subject is a human.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered orally and another being administered i.v.

Examples of additional medicaments include an antibacterial agent, antifungal agent, an antiviral agent, an anti-inflammatory agent and an anti-allergic agent.

Some embodiments include co-administration of a compound, composition or pharmaceutical composition described herein with an antibacterial agent such as a β-lactam. Examples of such β-lactams include Amoxicillin, Ampicillin (e.g., Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (e.g., Dicloxacillin, Flucloxacillin), Oxacillin, Methicillin, Nafcillin, Faropenem, Biapenem, Doripenem, Ertapenem, Imipenem, Meropenem, Panipenem, Tomopenem, Razupenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, CXA-101, RWJ-54428, MC-04, 546, ME1036, BAL30072, SYN 2416, Ceftiofur, Cefquinome, Cefovecin, Aztreonam, Tigemonam, Carumonam, RWJ-442831, RWJ-333441, and RWJ-333442.

Preferred embodiments include β-lactams such as Tebipenem, Tebipenem pivoxil, Apapenem, Ceftazidime, Biapenem, Doripenem, Ertapenem, Imipenem, Meropenem, ME1036, Tomopenem, Razupenem, and Panipenem.

Some embodiments include co-administration of the compounds, compositions and/or pharmaceutical compositions described herein with an additional agent, wherein the additional agent comprises a monobactam. Examples of monobactams include aztreonam, tigemonam, BAL 30072, SYN 2416 (BAL19764), and carumonam.

Some embodiments include co-administration of the compounds, compositions and/or pharmaceutical compositions described herein with an additional agent, wherein the additional agent comprises a Class A, B, C, or D beta-lactamase inhibitor. An example of a class B beta lactamase inhibitor includes ME1071 (Yoshikazu Ishii et al, "In Vitro Potentiation of Carbapenems with ME1071, a Novel Metallo-β-Lactamase Inhibitor, against Metallo-β-lactamase Producing *Pseudomonas aeruginosa* Clinical Isolates." Antimicrob. Agents Chemother. doi:10.1128/AAC.01397-09 (July 2010)). Other examples of beta-lactamase inhibitors administered as an additional agent include clavulanic acid, tazobactam, sulbactam, avibactam (NXL-104), MK-7655, and BAL29880. MK-7655 has the following structure:

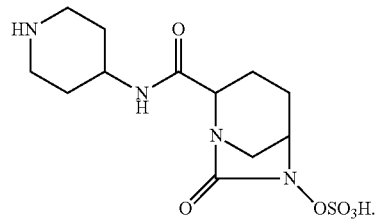

MK-7655

Indications

The compounds and compositions comprising cyclic boronic acid ester derivatives described herein can be used to treat bacterial infections. Bacterial infections that can be treated with the compounds, compositions and methods described herein can comprise a wide spectrum of bacterial species. Example organisms include gram-positive bacteria, gram-negative bacteria, aerobic and anaerobic bacteria, such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella* and other organisms.

More examples of bacterial infections include *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vul-*

*garis, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus subsp. hyicus, Staphylococcus haemolyticus, Staphylococcus hominis*, or *Staphylococcus saccharolyticus*.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

EXAMPLES

General Procedures

Materials used in preparing the cyclic boronic acid ester derivatives described herein may be made by known methods or are commercially available. It will be apparent to the skilled artisan that methods for preparing precursors and functionality related to the compounds claimed herein are generally described in the literature including, for example, procedures described in U.S. Pat. No. 7,271,186 and WO2009064414, each of which is incorporated by reference in its entirety. In these reactions, it is also possible to make use of variants which are themselves known to those of ordinary skill in this art, but are not mentioned in greater detail. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March Advanced Organic Chemistry (Wiley), Carey and Sundberg, Advanced Organic Chemistry (incorporated herein by reference in their entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts Protecting Groups in Organic Synthesis, 4th Ed., John Wiley & Sons (2007), incorporated herein by reference in its entirety.

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

The following abbreviations have the indicated meanings:

DCM=dichloromethane

DMF=N,N-dimethylformamide

ESBL=extended-spectrum β-lactamase

EtOAc=ethyl acetate

HATU=2-(7-aza-1H-benzotriazole-1-yl)-1,1,3,3-tetramethyluronium hexafluorophosphate MeCN=acetonitrile MIC=minimum inhibitory concentration NMR=nuclear magnetic resonance r.t.=room temperature TBDMSCl=tert-butyldimethylsilyl chloride TBS=tert-butyldimethylsilyl TFA=trifluoroacetic acid THF=tetrahydrofuran TLC=thin layer chromatography The following example schemes are provided for the guidance of the reader, and collectively represent an example method for making the compounds provided herein. Furthermore, other methods for preparing compounds described herein will be readily apparent to the person of ordinary skill in the art in light of the following reaction schemes and examples. Unless otherwise indicated, all variables are as defined above.

Illustrative Compound Examples

Example 1

2-(METHYLTHIO)-N-((2R,6S)-8-OXO-9,10-DI-OXA-1-BORABICYCLO[4.3.1]DEC-4-EN-2-YL) ACETAMIDE (1)

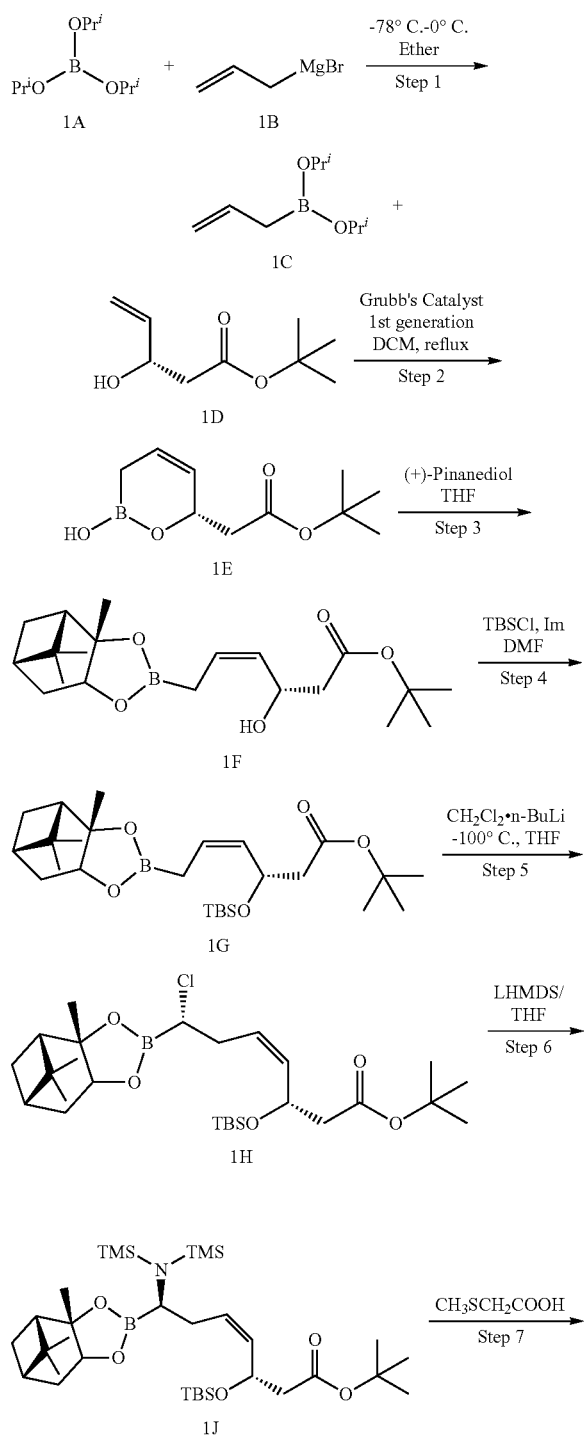

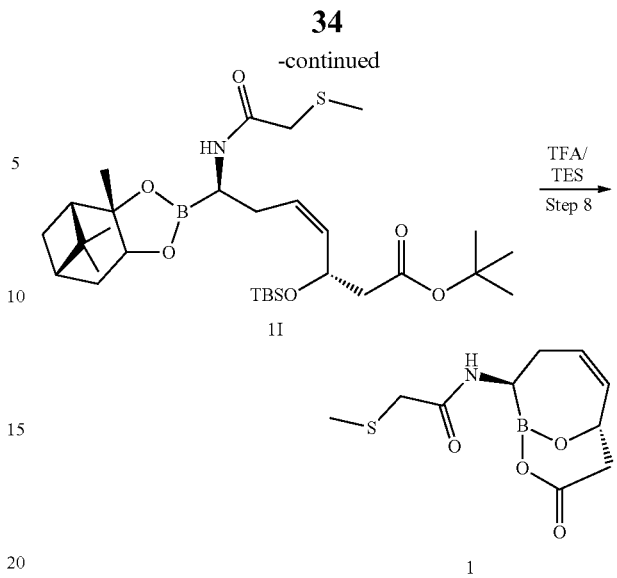

Step 1: Synthesis of 1C

A 3 L three-neck round-bottom flask equipped with addition funnel, thermometer and mechanical stirrer was charged with triisopropyl borate 1A (153.5 g, 0.816 mol) and ether (1 L) under nitrogen. The flask was cooled to −78° C. and allylmagnesium bromide 1B (800 mL, 0.80 mol, 1M in ether) was added via addition funnel over 1 hour with vigorous stirring. The resulting reaction mixture was slowly warmed up to 0° C. over 2 hours, and allowed to stay at 0° C. for another 1 hour. The reaction mixture was then cooled below −70° C. and hydrogen chloride solution (408 mL, 0.816 mol, 2.0 M in ether) was added via the addition funnel in 25 min. After addition was completed, the bath was removed and the mixture was slowly warmed up to room temperature in 1.5 hours. After reaching room temperature, the stirring was stopped and the mixture was allowed to settle down. The top clear solution was decanted and the remaining grey solid was washed with ether (500 mL×2) and filtered through Celite. The ether solution was concentrated and the top layer was decanted from bottom viscous orange layer. The top layer was distilled under reduced pressure (~10 mmHg) to give a clear colorless liquid 1C (103 g, 75% yield).

Step 2: Synthesis of 1E

A 1 L round-bottom flask equipped with a condenser under nitrogen was charged with the alcohol 1D (41.6 g, 0.24 mol) (*Synlett*, 2011, 20, 3002-3004, which is incorporated herein by reference in its entirety), borate 1C (103 g, 0.60 mol) and CH$_2$Cl$_2$ (800 mL). Grubbs catalyst (13.7 g, 0.016 mol) was added to the solution at room temperature. The reaction mixture was degassed and filled with nitrogen (three times). The flask was put into 50° C. oil bath, refluxing for 18 hours. After cooling down, the dark solution was concentrated and directly purified by column chromatography eluting with hexanes/ethyl acetate (5/1 to 2/1) to give impure product as dark oil 1E (60.2 g)

Step 3: Synthesis of 1F

In a round bottom flask containing a solution of boron compound 1E (60.2 g, impure, 0.24 mol) in THF (600 mL) at room temperature were added (+)-pinanediol (62.6 g, 0.37 mol). The reaction mixture was stirred at room temperature for 16 hours with NMR monitoring showing the completion of reaction. The solution was concentrated to dryness. The residual dark oil was purified by column chromatography eluting with hexanes/ethyl acetate (8/1 to 3/1) to give a brown oil 1F (73.7 g, 83% in two steps).

Step 4: Synthesis of 1G

In a round bottom flask containing a solution of pinacol borate alcohol 1F (73.7 g, 202 mmol) in DMF (200 mL) was added TBSCl (61.0 g, 404 mmol) at room temperature (Note 1), followed by imidazole (41.3 g, 606 mmol). After stirring at room temperature for 20 hour (Note 2), TLC shows the completion of reaction. The reaction mixture was diluted with DCM (600 mL) and washed with water (800 mL, 3 times). A mixture of hexanes/ethyl acetate (1/1, v/v) was used to extract the aqueous layer in sequence. The combined organic layers were dried ($Na_2SO_4$), filtered and concentrated to dryness. The residual oil was purified by column chromatography eluting with hexanes/ethyl acetate (30/1 to 5/1) to give a slightly yellow oil 1G (86.0 g, 87%).

Step 5: Synthesis of 1H

In a three-neck round bottom flask equipped with a thermometer and magnetic stir bar was charged with THF (700 mL) and $CH_2Cl_2$ (22.6 mL, 353 mmol) under nitrogen. The solution was cooled to −95° C. and was added a solution of BuLi (85 mL, 212 mmol) via syringe along the sides of the flask and keeping the internal temperature<−90° C. Upon completion of the addition, the reaction mixture was stirred at −95° C. for 40 minutes. A solution of pinanediol boronate 1G (86.0 g, 176 mmol) in THF (200 mL) was added to the solution of dichloromethyllithium via cannula keeping the temperature<−90° C. Upon completion of the addition, the reaction mixture was then allowed to warm to room temperature slowly. After stirring at room temperature overnight, the reaction mixture was quenched with saturated solution of $NH_4Cl$ (1 L). The mixture was extracted with hexanes/ethyl acetate (1/1, v/v, 2×800 mL). The combined organic layers were washed with brine, dried ($Na_2SO_4$), filtered and concentrated to dryness. The residual oil was purified by column chromatography eluting with hexanes/ethyl acetate (20/1 to 6/1) to give a slightly yellow oil 1H (82.2 g, 86%, note 7).

Step 6: Synthesis of 1J

To a solution of compound 1H (3.43 g, 6.5 mmol) in anhydrous THF (30 mL) at −78° C. was added drop-wise LHMDS (1.0 M in hexane, 7.8 mL, 7.8 mmol) over 20 min, the mixture was stirred at this temperature for 0.5 h, and then warmed up slowly to r.t. and stirred at 30° C. for 1 h to afford compound 1J in THF solution which was used directly without any workup (6.5 mmol, 100%).

Step 7: Synthesis of 1I

To a solution of 2-(methylthio)acetic acid (892 mg, 8.42 mmol) in DMF/THF (15 mL/30 mL) was added HATU (3.21 g, 8.42 mmol), the mixture was stirred at r.t. for 10 min, then compound 1J in THF solution (30 mL, 6.5 mmol) was added and the mixture was stirred at 30° C. overnight, evaporated to small volume, extracted with EA/PE=1:1, washed with water and brine, dried over $Na_2SO_4$, filtered and evaporated to dryness, purified by silica gel chromatography to afford compound 1I (2.36 g, 61%).

Step 8: Synthesis of 1

A solution of compound 1I (565 mg, 0.95 mmol) in TFA (90%)(30 mL)/TES (1.1 g, 9.5 mmol) was stirred at room temperature for 18 h, evaporated to dryness and co-evaporated with MeCN and then toluene. Then the residue was dissolved in EtOAc, purified by silica gel chromatography (EtOAc then EtOAc/MeOH 20/1) to give Compound 1 as a white solid (175 mg, 67% yield).

$^1$H NMR (300 MHz, $CD_3OD$) δ 5.65-5.58 (m, 1H), 5.37 (dt, 1H), 4.93-4.96 (m, 1H), 3.47 (s, 2H), 2.95-2.87 (m, 2H), 2.53-2.45 (m, 2H), 2.43-2.32 (m, 1H), 2.21 (s, 3H).

MS calculated for ($C_{10}H_{14}BNO_4S$): 255.
MS (ESI, positive) found: (M+1): 256.
MS (ESI, negative) found: (M−1): 254.

Example 2

2-(CYANOMETHYLTHIO)-N-((2R,6S)-8-OXO-9,10-DIOXA-1-BORABICYCLO[4.3.1]DEC-4-EN-2-YL)ACETAMIDE (2)

Compound 2 was prepared as described in Example 1 (steps 1-8) except replacing 2-(methylthio)acetic acid in step 7 with (cyanomethylthio)acetic acid.

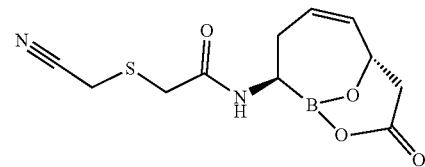

$^1$H NMR (400 MHz, $CD_3OD$) δ 5.72 (s, 1H), 5.37 (d, 1H), 4.92-4.96 (m, 1H), 3.60-3.80 (m, 4H), 2.87-2.79 (m, 2H), 2.54-2.29 (m, 2H), 2.40-2.29 (m, 1H).

MS calculated for ($C_{11}H_{13}BN_2O_4S$): 280.
MS (ESI, positive) found: (M+1): 281.
MS (ESI, negative) found: (M−1): 279.

Example 3

2-(DIFLUOROMETHYLTHIO)-N-((2R,6S)-8-OXO-9,10-DIOXA-1-BORABICYCLO[4.3.1]DEC-4-EN-2-YL)ACETAMIDE (3)

Compound 3 was prepared as described in Example 1 (steps 1-8) except replacing 2-(methylthio)acetic acid in step 7 with (difluoromethylthio)acetic acid.

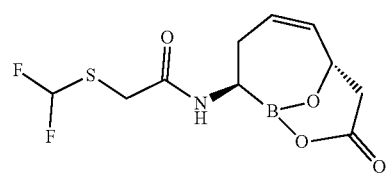

$^1$H NMR (400 MHz, $CD_3OD$) δ 7.18 (t, 1H), 5.70 (d, 1H), 5.37 (d, 1H), 3.89 (s, 2H), 2.80 (dd, 2H), 2.51-2.31 (m, 2H), 2.31-2.25 (m, 1H).

MS calculated for ($C_{10}H_{12}BF_2NO_4S$): 291.
MS (ESI, positive) found: (M+1): 292.
MS (ESI, negative) found: (M−1): 290.

Example 4

2-(1-METHYL-1H-TETRAZOL-5-YLTHIO)-N-((2R,6S)-8-OXO-9,10-DIOXA-1-BORABICYCLO[4.3.1]DEC-4-EN-2-YL)ACETAMIDE (4)

Compound 4 was prepared as described in Example 1 (steps 1-8) except replacing 2-(methylthio)acetic acid in step 7 with (1-methyl-1H-tetrazol-5-ylthio)acetic acid.

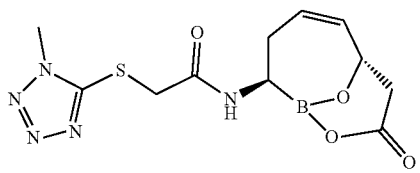

4

¹H NMR (400 MHz, CD₃OD) δ 5.67 (m, 1H), 5.48 (d, 1H), 4.34 (s, 2H), 3.99 (s, 3H), 2.81-2.75 (m, 2H), 2.42-2.38 (m, 2H), 2.25-2.22 (m, 1H).
MS calculated for ($C_{11}H_{14}BN_5O_4S$): 323.
MS (ESI, positive) found: (M+1): 324.
MS (ESI, negative) found: (M−1): 322.

Example 5

2-(4-METHYL-4H-1,2,4-TRIAZOL-3-YLTHIO)-N-((2R,6S)-8-OXO-9,10-DIOXA-1-BORABICYCLO[4.3.1]DEC-4-EN-2-YL)ACETAMIDE (5)

Compound 5 was prepared as described in Example 1 (steps 1-8) except replacing 2-(methylthio)acetic acid in step 7 with (4-methyl-4H-1, 2, 4-triazol-3-ylthio)acetic acid.

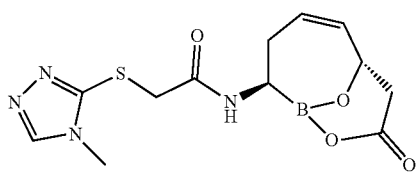

5

¹H NMR (400 MHz, CD₃OD) δ 8.68 (s, 1H), 5.68 (m, 1H), 5.35 (m, 1H), 4.16 (s, 2H), 3.73 (s, 3H), 2.81-2.73 (m, 2H), 2.44-2.21 (m, 4H).
MS calculated for ($C_{12}H_{17}BN_4O_5S$): 322.
MS (ESI, positive) found: (M+1): 323.
MS (ESI, negative) found: (M−1): 321.

Example 6

2-(5-AMINO-1,3,4-THIADIAZOL-2-YLTHIO)-N-((2R,6S)-8-OXO-9,10-DIOXA-1-BORABICYCLO[4.3.1]DEC-4-EN-2-YL)ACETAMIDE (6)

Compound 6 was prepared as described in Example 1 (steps 1-8) except replacing 2-(methylthio)acetic acid in step 7 with (5-amino-1, 3, 4-thiadiazol-2-ylthio)acetic acid.

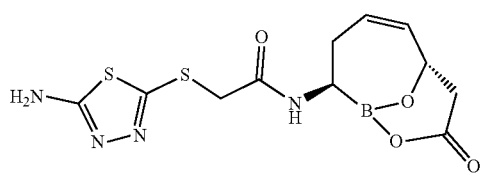

6

¹H NMR (400 MHz, CD₃OD) δ 5.72 (m, 1H), 5.37 (d, 1H), 4.07 (s, 2H), 2.82-2.76 (dd, 2H), 2.51-2.28 (m, 2H0, 2.24-2.02 (m, 1H).

MS calculated for ($C_{11}H_{13}BN_4O_4S_2$): 340.
MS (ESI, positive) found: (M+1): 341.
MS (ESI, negative) found: (M−1): 339.

Example 7

2-(1,3,4-THIADIAZOL-2-YLTHIO)-N-((2R,6S)-8-OXO-9,10-DIOXA-1-BORABICYCLO[4.3.1]DEC-4-EN-2-YL)ACETAMIDE (7)

Compound 7 was prepared as described in Example 1 (steps 1-8) except replacing 2-(methylthio)acetic acid in step 7 with (1, 3, 4-thiadiazol-2-ylthio)acetic acid.

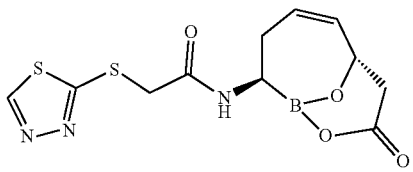

7

¹H NMR (400 MHz, CD₃OD) δ 9.38 (s, 1H), 5.71 (t, 1H), 5.37 (d, 1H), 4.43 (s, 2H), 3.29 (dd, 2H), 2.81-2.77 (m, 2H), 2.49-2.42 (m, 2H), 2.24-2.14 (s, 1H).
MS calculated for ($C_{11}H_{12}BN_3O_4S_2$): 325.
MS (ESI, positive) found: (M+1): 326.
MS (ESI, negative) found: (M−1): 324.

Example 8

2-(5-METHYL-1,3,4-THIADIAZOL-2-YLTHIO)-N-((2R,6S)-8-OXO-9,10-DIOXA-1-BORABICYCLO[4.3.1]DEC-4-EN-2-YL)ACETAMIDE (8)

Compound 8 was prepared as described in Example 1 (steps 1-8) except replacing 2-(methylthio)acetic acid in step 7 with (5-methyl-1, 3, 4-thiadiazol-2-ylthio)acetic acid.

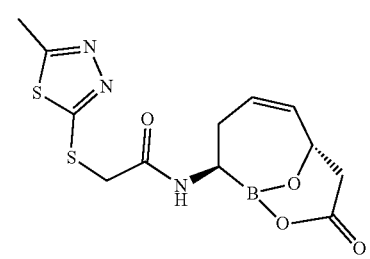

8

¹H NMR (400 MHz, CD₃OD) δ 5.73-5.68 (m, 1H), 5.34 (d, 1H), 5.20 (s, 1H), 4.34 (s, 2H), 2.82-2.71 (m, 5H), 2.55-2.43 (m, 2H), 2.22-2.18 (m, 1H).
MS calculated for ($C_{12}H_{14}BN_3O_4S_2$): 339.
MS (ESI, positive) found: (M+1): 340.
MS (ESI, negative) found: (M−1): 338.

Example 9

Potentiation of Aztreonam

The potency and spectrum of β-lactamase inhibitors (BLIs) was determined by assessing their aztreonam potentiation activity in a dose titration potentiation assay using strains of various bacterial species that are resistant to aztreonam due to expression of various β-lactamases. Aztreonam is a monobactam antibiotic and is hydrolyzed by the majority of beta-lactamases that belong to class A or C (but not class B or D). The potentiation effect was observed as the ability of BLI compounds to inhibit growth in the presence of sub-inhibitory concentration of aztreonam. MICs of test strains varied from 64 µg/mL to >128 µg/mL. Aztreonam was present in the test medium at 4 µg/mL. Compounds were tested at concentrations up to 40 µg/mL. In this assay the potency of compounds was reported as the minimum concentration of BLI required to inhibit bacterial growth in the presence of 4 µg/mL of aztreonam ($MPC_{@4}$). Table 1 summarizes the BLI potency of aztreonam potentiation ($MPC_{@4}$) for various strains overexpressing class A (ESBL and KPC), and class C beta-lactamases. Aztreonam MIC for each strain is also shown.

TABLE 1

Activity of BLIs to potentiate aztreonam against strains expressing class A and class C enzymes.

| | Aztreonam MIC (µg/mL) | | | | | | | |
|---|---|---|---|---|---|---|---|---|
| | >128 | >128 | >128 | 64 | 128 | >128 | 64 | >128 |
| Strain | CTX-M-14 | CTX-M-15 | SHV-5 | SHV-12 | TEM-10 | KPC-2 | | CMY-6 |
| β-lactamase | KP1005 | KP1009 | ec308 | KP1010 | ec302 | KP1004 | ECL1002 | EC1010 |
| Tazobactam | Y | Y | Y | X | X | Z | Z | Y |
| Clavulanic Acid | X | X | X | X | X | Z | Z | Z |
| Compound 1 | X | X | X | X | X | X | X | X |
| Compound 2 | X | X | X | X | X | X | X | X |
| Compound 3 | X | X | X | X | X | X | X | X |
| Compound 4 | X | X | X | X | X | X | X | X |
| Compound 5 | X | X | X | X | Y | Y | X | X |
| Compound 6 | X | X | X | X | X | X | X | X |
| Compound 7 | X | X | X | X | X | X | X | X |
| Compound 8 | X | Y | X | X | X | Y | X | Y |

X = $MPC_{@4}$ ≤ 5 µg/mL;
Y = 5 µg/mL < $MPC_{@4}$ ≤ 20 µg/mL;
Z = $MPC_{@4}$ > 20 µg/mL

Example 10

Potentiation of Tigemonam

Selected β-lactamase inhibitors were also tested for their ability to potentiate the monobactam tigemonam. The potentiation effect was observed as the ability of BLI compounds to inhibit growth in the presence of sub-inhibitory concentration of tigemonam. MICs of test strains varied from 16 µg/mL to >64 µg/mL. Tigemonam was present in the test medium at 4 µg/mL. Compounds were tested at concentrations up to 40 µg/mL. In this assay the potency of compounds was reported as the minimum concentration of BLI required to inhibit bacterial growth in the presence of 4 µg/mL of aztreonam ($MPC_{@4}$). Table 2 summarizes the BLI potency of tigemonam potentiation ($MPC_{@4}$) for various strains overexpressing class A (ESBL) and class C beta-lactamases. Tigemonam MIC for each strain is also shown.

TABLE 2

Activity of BLIs to potentiate tigemonam against strains expressing class A and class C enzymes.

| | Tigemonam MIC (µg/mL) | | | | | | |
|---|---|---|---|---|---|---|---|
| | >64 | >64 | >64 | >64 | >64 | 32 | 16 |
| Strain | CTX-M-14 | CTX-M-15 | SHV-5 | SHV-12 | TEM-10 | | CMY-6 |
| β-lactamase | KP1005 | KP1009 | ec308 | KP1010 | ec302 | ECL1002 | EC1010 |
| Tazobactam | Y | Y | X | X | X | Y | X |
| Clavulanic Acid | X | X | X | X | X | Y | Y |
| Compound 1 | X | X | X | X | Y | X | X |
| Compound 2 | X | X | X | X | Y | X | X |
| Compound 3 | X | X | X | X | Y | X | X |
| Compound 4 | Y | X | X | X | Y | X | X |
| Compound 5 | X | X | X | X | Z | X | X |

TABLE 2-continued

Activity of BLIs to potentiate tigemonam against strains expressing class A and class C enzymes.

| | Tigemonam MIC (µg/mL) | | | | | | |
|---|---|---|---|---|---|---|---|
| | >64 | >64 | >64 | >64 | >64 | 32 | 16 |
| Compound 6 | X | X | X | X | Y | X | X |
| Compound 7 | X | X | X | X | Y | X | X |
| Compound 8 | Y | X | Y | X | Y | X | X |

X = $MPC_{@4}$ ≤ 5 µg/mL;
Y = 5 µg/mL < $MPC_{@4}$ ≤ 20 µg/mL;
Z = $MPC_{@4}$ > 20 µg/mL

Example 11

Potentiation of Biapenem

β-lactamase inhibitors were also tested for their ability to potentiate the carbapenem biapenem against strains producing class A (KPC) and class D (OXA-48) carbapenemases. The potentiation effect was observed as the ability of BLI compounds to inhibit growth in the presence of a sub-inhibitory concentration of biapenem. Biapenem MIC of test strains were 16-32 µg/mL. Biapenem was present in the test medium at 1 µg/mL. Compounds were tested at concentrations up to 40 µg/mL. In this assay the potency of compounds was reported as the minimum concentration of BLI required to inhibit bacterial growth in the presence of 1 µg/mL of biapenem ($MPC_{@1}$). Table 3 summarizes the BLI potency of biapenem potentiation ($MPC_{@1}$) for two strains overexpressing class A (KPC) and class D (OXA-48) carbapenemases. Biapenem MIC for each strain is also shown.

TABLE 3

Activity of BLIs to potentiate biapenem against strains expressing class A (KPC) or class D (OXA-48) carbapenemases.

| Biapenem MIC (µg/mL) | 32 | 16 |
|---|---|---|
| Strain | KPC-2 | OXA-48 |
| β-lactamase | KP1004 | KP1086 |
| Tazobactam | Z | Y |
| Clavulanic Acid | Y | Z |

TABLE 3-continued

Activity of BLIs to potentiate biapenem against strains expressing class A (KPC) or class D (OXA-48) carbapenemases.

| Biapenem MIC (µg/mL) | 32 | 16 |
|---|---|---|
| Compound 1 | X | Z |
| Compound 2 | X | Z |
| Compound 3 | X | Z |
| Compound 4 | X | Z |
| Compound 5 | X | Z |
| Compound 6 | X | Z |
| Compound 7 | X | Z |
| Compound 8 | X | Z |

X = $MPC_{@1}$ ≤ 5 µg/mL;
Y = 5 µg/mL < $MPC_{@1}$ ≤ 20 µg/mL;
Z = $MPC_{@1}$ > 20 µg/mL

Example 12

Inhibitory Activity $K_i$ values of inhibition of purified class A, C and D enzymes were determined spectrophotometrically using nitrocefin as reporter substrate. Purified enzymes were mixed with various concentrations of inhibitors in reaction buffer and incubated for 10 min at room temperature. Nitrocefin was added and substrate cleavage profiles were recorded at 490 nm every 10 sec for 10 min. The results of these experiments are presented in Table 4. These experiments confirmed that the described compounds are inhibitors with a broad-spectrum of activity towards various β-lactamases.

TABLE 4

Activity of BLIs ($K_i$, µM) to inhibit cleavage of nitrocefin by purified class A, C and D enzymes

| | $K_i$ CTX-M-14, NCF, µM | $K_i$ SHV-12, NCF, µM | $K_i$ TEM-10, NCF, µM | $K_i$ KPC-2, NCF, µM | $K_i$ P99, NCF, µM | $K_i$ CMY-2, NCF, µM | $K_i$ OXA-48, NCF, µM |
|---|---|---|---|---|---|---|---|
| Tazobactam | X | X | X | Z | Z | Y | Y |
| Clavulanic Acid | X | X | X | Z | Z | Z | Z |
| Compound 1 | X | X | X | Y | X | X | X |
| Compound 2 | X | X | X | Y | X | X | Y |
| Compound 3 | X | X | X | Y | X | ND | X |
| Compound 4 | X | X | X | Y | X | X | X |
| Compound 5 | X | X | X | Y | X | X | Y |
| Compound 6 | X | X | X | Y | X | X | Y |

TABLE 4-continued

Activity of BLIs ($K_i$, µM) to inhibit cleavage of
nitrocefin by purified class A, C and D enzymes

| | $K_i$ CTX-M-14, NCF, µM | $K_i$ SHV-12, NCF, µM | $K_i$ TEM-10, NCF, µM | $K_i$ KPC-2, NCF, µM | $K_i$ P99, NCF, µM | $K_i$ CMY-2, NCF, µM | $K_i$ OXA-48, NCF, µM |
|---|---|---|---|---|---|---|---|
| Compound 7 | X | X | X | Y | X | X | X |
| Compound 8 | X | X | X | Y | X | X | X |

X = $K_i \leq 0.1$ µM;
Y = $0.1$ µM $< K_i \leq 1$ µM;
Z = $K_i > 1$ µM;
ND = not determined Example 13

Mexab-Oprm Dependent Efflux of Blis

Efflux of BLIs from *Pseudomonas aeruginosa* by the MexAB-OprM efflux pump was also evaluated. The plasmid expressing the gene encoding KPC-2 was introduced into two strains of *P. aeruginosa*, PAM1032 and PAM1154 that overexpressed or lacked MexAB-OprM, respectively. Due to expression of KPC-2 both strains became resistant to biapenem. Biapenem is not affected by efflux in *P. aeruginosa* and both strains had the same biapenem MIC of 32 µg/ml. Potency of BLIs to potentiate biapenem in these strains was determined. Potency was defined as the ability of BLI to decrease MIC of biapenem 64-fold, from 32 µg/ml to 0.5 µg/ml, or $MPC_{64}$. The ratio of $MPC_{64}$ values for each BLI in PAM1032/KPC-2 (efflux proficient) and PAM1154/KPC-2 (efflux deficient) was determined to generate the Efflux Index (EI). The results are shown in Table 5.

TABLE 5

MexAB-OprM Dependent Efflux of BLIs from *P. aeruginosa*

| | PAM1032/ KPC-2 Biapenem $MPC_{64}$ | PAM1154/ KPC-2 Biapenem $MPC_{64}$ | EI |
|---|---|---|---|
| Compound 1 | 80 | 5 | 16 |
| Compound 2 | 80 | 5 | 16 |
| Compound 3 | >80 | 5 | >16 |
| Compound 4 | >80 | 10 | >8 |
| Compound 5 | 80 | 20 | 4 |
| Compound 6 | 40 | 5 | 8 |
| Compound 7 | 40 | 5 | 8 |

Example 14

Oral Pharmacokinetics

Several compounds were tested for their oral pharmacokinetics. Rats (n=3 per compound) were administered a single oral dose. Oral doses were administered as a bolus. Plasma (~0.3 mL) samples were collected from each rat at designated time points up to 24 hours. Blood samples were centrifuged within 5 min of collection at 12000 g for 5 min to obtain plasma. The plasma samples were stored at −80° C. until analyzed. Data were analyzed using WinNonlin. The results are presented in Table 6.

TABLE 6

Bioavailability of BLIs

| Compound | Dose (mg/kg) | Range of % Oral Bioavailability |
|---|---|---|
| 1 | 300 | 61-77 |
| 1 | 100 | 63-74 |
| 1 | 30 | 44-61 |
| 3 | 30 | 28-54 |
| 4 | 50 | 3.2-4.6 |
| 5 | 50 | 2.5-3 |
| 6 | 30 | 2-4 |

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials that are susceptible to modifications, as well as alterations in the fabrication methods and equipment. Such modifications will become apparent to those skilled in the art from a consideration of this disclosure or practice of the methods disclosed herein. Consequently, it is not intended that this invention be limited to the specific embodiments disclosed herein, but that it cover all modifications and alternatives coming within the true scope and spirit of the invention.

What is claimed is:
1. A compound having the structure of formula Ia or formula Ib:

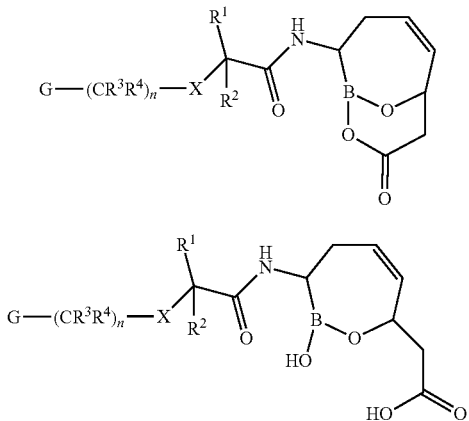

Ia

Ib or a pharmaceutically acceptable salt thereof, wherein:
$R^1$ and $R^2$ are independently selected from the group consisting of —H, —OH, halo, optionally substituted $C_{1-10}$ alkoxy, optionally substituted $C_{1-10}$ alkyl, optionally substituted $C_{2-10}$ alkenyl, optionally substituted $C_{2-10}$ alkynyl, optionally substituted $C_{3-7}$ carbocyclyl, optionally substituted 3-8 membered heterocyclyl, optionally substituted $C_{6-10}$ aryl, and optionally substituted 5-10 membered heteroaryl, or alternatively $R^1$ and $R^2$ are taken together with the carbon atom to which they are attached to form an optionally substituted $C_{3-6}$ carbocyclyl or an optionally substituted 3-6 membered heterocyclyl;

each $R^3$ and $R^4$ are independently selected from the group consisting of —H, —OH, halo, optionally substituted $C_{1-10}$ alkoxy, optionally substituted $C_{1-10}$ alkyl, optionally substituted $C_{2-10}$ alkenyl, optionally substituted $C_{2-10}$ alkynyl, optionally substituted $C_{3-7}$ carbocyclyl, optionally substituted 3-8 membered heterocyclyl, optionally substituted $C_{6-10}$ aryl, and optionally substituted 5-10 membered heteroaryl, or alternatively $R^3$ and $R^4$ in each $CR^3R^4$ unit are taken together with the carbon atom to which they are attached to form an optionally substituted $C_{3-6}$ carbocyclyl or an optionally substituted 3-6 membered heterocyclyl;

X is selected from the group consisting of —S—, —S(O)—, —S(O)$_2$—, —O—, and —NR$^7$—;

G is selected from the group consisting of —NR$^7$R$^8$, —N$_3$, —C(O)NR$^7$R$^8$, —S(O)$_2$NR$^7$R$^8$, —SR$^9$, —OR$^9$, —CH$_2$NR$^7$C(O)R$^1$, —C(=NOR$^9$)—Z, —C(O)OR$^9$, —C(O)NR$^7$(OR$^9$), —NR$^7$(OR$^9$), —NR$^7$C(O)R$^{10}$, —NR$^7$C(O)NR$^8$R$^{7a}$, —NR$^7$C(O)OR$^9$, —NR$^7$S(O)$_2$R$^9$, —NR$^7$S(O)$_2$NR$^8$R$^{7a}$, —NR$^7$NR$^8$R$^{7a}$, —C(O) NR$^7$NR$^8$R$^{7a}$, —S(O)$_2$NR$^7$NR$^8$R$^{7a}$, —C(=NR$^7$)R$^8$, —C(=NR$^7$)NR$^8$R$^{7a}$, —NR$^7$CR$^{10}$(=NR$^8$), —NR$^7$C(=NR$^8$)NR$^{7a}$R$^{8a}$, —CN, $C_{1-10}$ alkyl optionally substituted with one or more $R^{11}$, $C_{2-10}$ alkenyl optionally substituted with one or more $R^{11}$, $C_{2-10}$ alkynyl optionally substituted with one or more $R^{11}$, $C_{3-7}$ carbocyclyl optionally substituted with one or more $R^{11}$, 5-10 membered heterocyclyl optionally substituted with one or more $R^{11}$, $C_{6-10}$ aryl optionally substituted with one or more $R^{11}$, 5-10 membered heteroaryl optionally substituted with one or more $R^{11}$, $C_{3-7}$ carbocyclyl-$C_{1-6}$ alkyl optionally substituted with one or more $R^{11}$, 5-10 membered heterocyclyl-$C_{1-6}$ alkyl optionally substituted with one or more $R^{11}$, $C_{6-10}$ aryl-$C_{1-6}$ alkyl optionally substituted with one or more $R^{11}$, and 5-10 membered heteroaryl-$C_{1-6}$ alkyl optionally substituted with one or more $R^{11}$;

$R^7$, $R^{7a}$, $R^8$, and $R^{8a}$ are independently selected from the group consisting of H, —$C_{1-9}$ alkyl, —$C_{1-9}$ alkylR$^{10}$, —OR$^9$, —CH(=NH), optionally substituted $C_{6-10}$ aryl, optionally substituted 5-10 membered heteroaryl, optionally substituted $C_{3-10}$ carbocyclyl, and optionally substituted 3-10 membered heterocyclyl;

each $R^9$ is independently selected from the group consisting of H, $C_{1-9}$ alkyl, $C_{1-9}$ alkylR$^{10}$, optionally substituted $C_{6-10}$ aryl, optionally substituted 5-10 membered heteroaryl, optionally substituted $C_{3-10}$ carbocyclyl, and optionally substituted 3-10 membered heterocyclyl;

each $R^{10}$ is independently selected from the group consisting of optionally substituted $C_{6-10}$ aryl, optionally substituted 5-10 membered heteroaryl, optionally substituted $C_{3-10}$ carbocyclyl, and optionally substituted 3-10 membered heterocyclyl;

$R^{11}$ is selected from the group consisting of $C_{1-4}$ alkyl, —OR$^9$, —$C_{1-6}$ alkyl-COOR$^9$, optionally substituted $C_{6-10}$ aryl, optionally substituted 5-10 membered heteroaryl, optionally substituted $C_{3-10}$ carbocyclyl, and optionally substituted 3-10 membered heterocyclyl, —SR$^9$, —NR$^7$R$^8$, halo, —CN, —C(O)NR$^7$R$^8$, and —NR$^7$C(O)R$^{10}$;

Z is selected from the group consisting of optionally substituted $C_{6-10}$ aryl, optionally substituted $C_{3-10}$ carbocyclyl, optionally substituted 5-10 membered heteroaryl, optionally substituted 3-10 membered heterocyclyl, —CH$_2$Y, —CH(Y)$_2$, and —C(Y)$_3$;

Y is selected from the group consisting of halo, cyano, and azido; and n is an integer selected from the group consisting of 0, 1, and 2.

2. The compound of claim 1 having the structure of formula IIa or IIb:

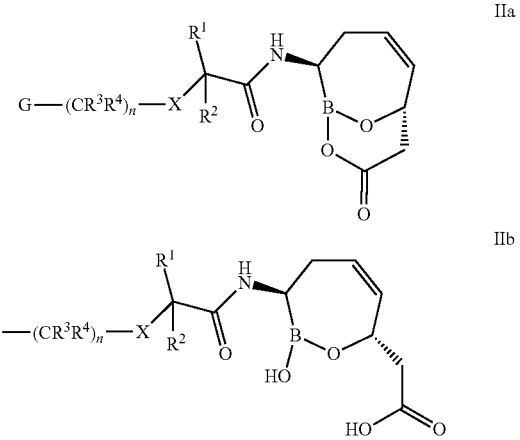

IIa

IIb or a pharmaceutically acceptable salt thereof.

3. The compound of claim 1, wherein X is —S—.

4. The compound of claim 1, wherein G is a heteroaryl optionally substituted with one or more $R^1$.

5. The compound of claim 1, wherein G is selected from the group consisting of $C_{1-4}$ alkyl, phenyl, imidazolyl, pyrazolyl, triazolyl, tetrazolyl, thiazolyl, thiadiazolyl, oxazolyl, oxadiazolyl, isoxazolyl, isothiazolyl, pyridinyl, pyrazinyl, pyrimidinyl, pyridazinyl, azetidinyl, and pyrazinyl, each optionally substituted by one or two $R^{11}$.

6. The compound of claim 1, wherein G is —$CH_3$.

7. The compound of claim 1, wherein G is —CN.

8. The compound of claim 1, wherein G is —$CHF_2$.

9. The compound of any of claim 1, wherein G is tetrazolyl optionally substituted with $R^{11}$.

10. The compound of claim 9, wherein G is 1-methyl-tetrazolyl.

11. The compound of claim 1, wherein G is triazolyl optionally substituted with one or two $R^{11}$.

12. The compound of claim 11, wherein G is 4-methyl-triazolyl.

13. The compound of claim 1, wherein G is thiadiazolyl optionally substituted with $R^{11}$.

14. The compound of claim 13, wherein G is 5-amino-1,3,4-thiadiazolyl.

15. The compound of claim 13, wherein G is 5-methyl-1,3,4-thiadiazolyl.

16. The compound of claim 1, wherein each $R^1$, $R^2$, $R^3$, and $R^4$ are independently selected from the group consisting of —H, —OH, halo, optionally substituted $C_{1-10}$ alkoxy, optionally substituted $C_{1-10}$ alkyl, optionally substituted $C_{2-10}$ alkenyl, optionally substituted $C_{2-10}$ alkynyl, optionally substituted $C_{3-7}$ carbocyclyl, optionally substituted 3-8 membered heterocyclyl, optionally substituted $C_{6-10}$ aryl, and optionally substituted 5-10 membered heteroaryl.

17. The compound of claim 1, wherein $R^1$ is H.

18. The compound of claim 1, wherein $R^2$ is H.

19. The compound of claim 1, wherein $R^3$ is H.

20. The compound of claim 1, wherein $R^4$ is H.

21. The compound of claim 1, wherein n is 1.

22. The compound of claim 1, wherein n is 0.

23. The compound of claim 1, wherein $R^1$, $R^2$, $R^3$ and $R^4$ are each H, and n is 1.

24. The compound of claim 1, having a structure selected from the group consisting of:

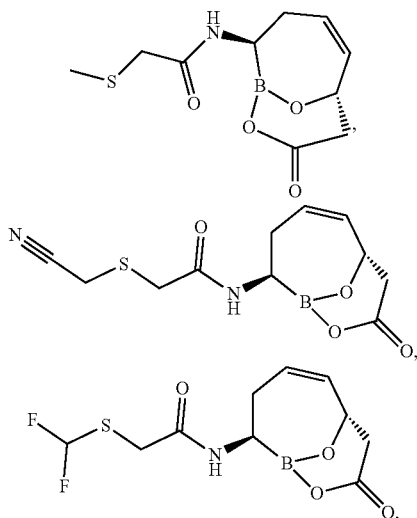

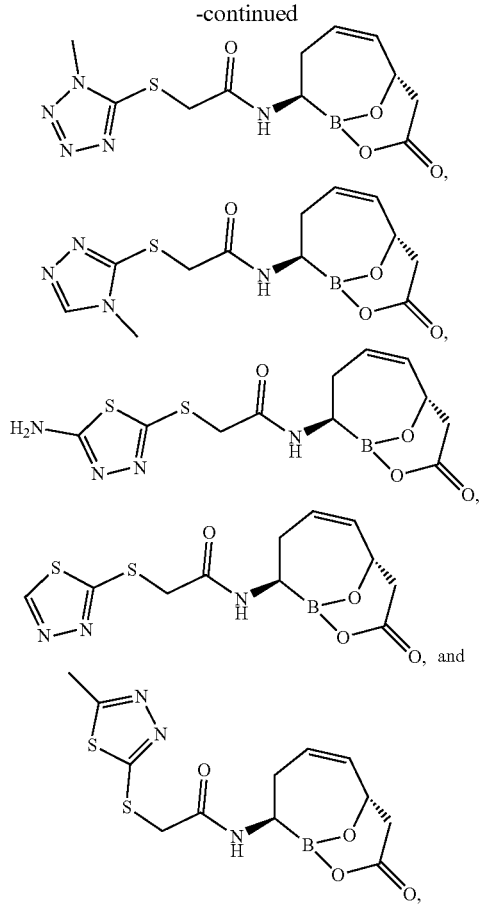

or a pharmaceutically acceptable salt thereof.

25. A pharmaceutical composition comprising a therapeutically effective amount of a compound according to claim 1 and a pharmaceutically acceptable excipient.

26. A method of therapeutically treating a bacterial infection, comprising administering to a subject in need thereof, a compound according to claim 1.

27. The method of claim 26, further comprising administering an additional medicament.

28. The method of claim 27, wherein the additional medicament is selected from an antibacterial agent, antifungal agent, an antiviral agent, an anti-inflammatory agent, or an anti-allergic agent.

29. The method of claim 28, wherein the additional medicament is a β-lactam.

30. The method of claim 29, wherein the β-lactam is selected from Amoxicillin, Ampicillin (Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (Dicloxacillin, Flucloxacillin), Oxacillin, Meticillin, Nafcillin, Faropenem, Biapenem, Doripenem, Ertapenem, Imipenem, Meropenem, Panipenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, Ceftiofur, Cefquinome, Cefovecin, Aztreonam, Tigemonam, or Carumonam.

31. The method of claim 29, wherein the β-lactam is selected from Tebipenem, Tebipenem pivoxil, Apapenem, Ceftazidime, Biapenem, Doripenem, Ertapenem, Imipenem, Meropenem, or Panipenem.

32. The method of claim 26, wherein the subject is a mammal.

33. The method of claim 32, wherein the mammal is a human.

34. The method of claim 26, wherein the infection comprises a bacterial species selected from *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

35. The method of claim 26, wherein the infection comprises a bacterial species selected from *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii,* or *Bacteroides splanchnicus.*

\* \* \* \* \*